US009202386B2

(12) United States Patent
Yuasa et al.

(10) Patent No.: US 9,202,386 B2
(45) Date of Patent: Dec. 1, 2015

(54) CENTER OF GRAVITY SHIFTING TRAINING SYSTEM

(75) Inventors: Shingo Yuasa, Osaka (JP); Hiroyuki Saito, Osaka (JP); Chiaki Yoshizuka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 13/822,816

(22) PCT Filed: Sep. 27, 2011

(86) PCT No.: PCT/JP2011/072030
§ 371 (c)(1),
(2), (4) Date: Mar. 13, 2013

(87) PCT Pub. No.: WO2012/043540
PCT Pub. Date: Apr. 5, 2012

(65) Prior Publication Data
US 2013/0171600 A1    Jul. 4, 2013

(30) Foreign Application Priority Data

Sep. 27, 2010  (JP) ................................. 2010-216220
Feb. 4, 2011  (JP) ................................. 2011-023067

(51) Int. Cl.
*G09B 19/00*     (2006.01)
*A61B 5/103*    (2006.01)
*A63B 69/36*    (2006.01)

(52) U.S. Cl.
CPC .............. *G09B 19/00* (2013.01); *A61B 5/1036* (2013.01); *A63B 2069/367* (2013.01)

(58) Field of Classification Search
CPC .... A61B 5/1036; A61B 5/1116; A61B 5/112; A61B 2562/0252; A63B 26/003; G09B 19/00
USPC .................................................. 434/247, 258
See application file for complete search history.

(56) References Cited

U.S. PATENT DOCUMENTS

| | | | |
|---|---|---|---|
| 5,654,810 A * | 8/1997 | Okamura et al. .................. 349/5 |
| 5,919,149 A * | 7/1999 | Allum ............................ 600/595 |
| 6,537,076 B2 * | 3/2003 | McNitt et al. ................. 434/252 |
| 2002/0127529 A1 * | 9/2002 | Cassuto et al. ................ 434/335 |

FOREIGN PATENT DOCUMENTS

| | | |
|---|---|---|
| JP | 07-275307 | 10/1995 |
| JP | 09-120464 | 5/1997 |
| JP | 2000-279464 | 10/2000 |

(Continued)

*Primary Examiner* — Peter Egloff
*Assistant Examiner* — Jerry-Daryl Fletcher
(74) *Attorney, Agent, or Firm* — Greenblum & Bernstein, P.L.C.

(57) ABSTRACT

A center of gravity shifting training system includes a display device having a display screen, a measurement device configured to measure a center of gravity position of the user, and a control device. The control device has a training mode and a setting mode of preparing setting data indicating a position of the target image in the display screen. In the setting mode, the control device performs estimation of a deviation of the center of gravity position based on the center of gravity position measured, and prepares the setting data indicating the position of the target image according to a result of the estimation. In the training mode, the control device displays the operation image on the screen in accordance with the center of gravity position measured, and displays the target image on the screen based on the setting data prepared through the setting mode.

11 Claims, 6 Drawing Sheets

(56) References Cited

FOREIGN PATENT DOCUMENTS

| | | |
|---|---|---|
| JP | 2003-79599 | 3/2003 |
| JP | 2004-41519 | 2/2004 |
| JP | 2007-000204 | 1/2007 |
| JP | 2009-259117 | 11/2009 |
| JP | 2009-277195 | 11/2009 |

* cited by examiner

CENTER OF GRAVITY SHIFTING TRAINING SYSTEM

TECHNICAL FIELD

The present invention relates to a center of gravity shifting training system which is used for training of center of gravity shifting for a user.

BACKGROUND ART

While one of important human motor functions is a function of center of gravity shifting, such function of center of gravity shifting may be deteriorated in a patient having a problem with body movement due to a disease or injury, or an elderly person, etc. Since a person who has an inadequate function of center of gravity shifting cannot make a smooth center of gravity shift such that the body weight is applied alternately to the left and right legs, for example, basic motion such as walking may be hindered. Therefore, center of gravity shifting training for enabling smooth center of gravity shifting is widely introduced in, for example, the field of rehabilitation.

On the other hand, there has been proposed a system which includes a measurement device (load detection means) disposed at the feet of a user (subject) and adapted for detecting the center of the total load applied to each leg of the user, wherein the system causes a display device to display an image showing the center of gravity position of the user evaluated from the output of the measurement device (see, for example, document 1, "JP 7-275307 A"). In the system described in document 1, a target icon (target image) which works as the target for center of gravity shifting is displayed on the display device, and the user is allowed to perform center of gravity shifting training to shift the center of gravity position in coordination with the movement of the target icon such that the image indicating the center of gravity position is overlapped on the target icon. Further, in the system described in document 1, a plurality of shifting patterns of the target icon are prestored in accordance with the training objective of the user so that the shifting pattern can be selected in accordance with the user.

In the system described in document 1, however, since a human selects a shifting pattern of the target icon from the plurality of shifting patterns prepared in advance, it is difficult to individually select a shifting pattern respectively suitable for each user when, for example, an unspecified large number of users are targeted. That is, the level of deterioration in the function of center of gravity shifting varies from person to person even among people having similar symptoms (for example, people whose function of the right leg is deteriorated), and it is not desirable to make all the users having similar symptoms perform rigidly uniform center of gravity shifting training from the viewpoint of the efficiency of training.

SUMMARY OF INVENTION

In view of the above insufficiency, the present invention has aimed to propose a center of gravity shifting training system capable of allowing a user to perform center of gravity shifting training suitable for the user.

The first aspect of the center of gravity shifting training system relating to the present invention includes: a display device having a display screen for displaying an image; a measurement device having a working face for receiving a load from a user and configured to measure a center of gravity position of the user in the working face; and a control device having two operation modes including a training mode in which an operation image which is shifted according to the center of gravity position measured at the measurement device and a target image which indicates a destination of the operation image are displayed on the display screen, and a setting mode in which setting data which indicates the position of the target image in the display screen is prepared. The control device includes: a mode switching unit configured to switch the operation mode of the control device between the training mode and the setting mode; an information acquisition unit configured to acquire the center of gravity position from the measurement device; a center of gravity position storage unit configured to store the center of gravity position acquired by the information acquisition unit during a setting period in which the operation mode of the control device is the setting mode; a deviation estimation unit configured to perform estimation of a deviation of the center of gravity position based on the center of gravity position stored in the center of gravity position storage unit; a setting determination unit configured to prepare the setting data indicating a position of the target image according to a result of the estimation by the deviation estimation unit; a setting data storage unit configured to store the setting data prepared at the setting determination unit; an operation processing unit configured to determine a display position of the operation image in the display screen according to the center of gravity position acquired by the information acquisition unit; and a display processing unit configured to display the operation image at the display position determined at the operation processing unit, and displaying the target image in the display screen based on the setting data stored in the setting data storage unit, in a training period in which the operation mode of the control device is the training mode.

As for the second aspect of the center of gravity shifting training system relating to the present invention, in addition to the first aspect, the control device includes a center of gravity shifting estimation unit. The center of gravity shifting estimation unit is configured to perform estimation of center of gravity shifting of the user based on a position of the operation image in the training period. The setting determination unit is configured to correct the setting data stored in the setting data storage unit according to a result of the estimation by the center of gravity shifting estimation unit.

As for the third aspect of the center of gravity shifting training system relating to the present invention, in addition to the first or second aspect, the display processing unit is configured to display the center of gravity position stored in the center of gravity position storage unit on the display screen in the setting period.

As for the fourth aspect of the center of gravity shifting training system relating to the present invention, in addition to the second aspect, the control device includes a comparison unit and a presentation unit. The comparison unit is configured to perform a comparison between a result of a current estimation by the center of gravity shifting estimation unit and a result of a previous estimation by the center of gravity shifting estimation unit. The presentation unit is configured to present a result of the comparison by the comparison unit.

As for the fifth aspect of the center of gravity shifting training system relating to the present invention, in addition to the fourth aspect, the comparison unit is configured to represent the result of the comparison by a numerical value. The presentation unit is configured to display the result of the comparison on the display screen.

As for the sixth aspect of the center of gravity shifting training system relating to the present invention, in addition to the first aspect, the control device includes a history creation unit, an operation storage unit, and a presentation unit. The history creation unit is configured to create an operation history indicating a history of position and movement of the operation image based on a position of the operation image determined at the operation processing unit in the training period. The operation storage unit is configured to store the operation history created at the history creation unit. The presentation unit is configured to present the operation history stored in the operation storage unit.

As for the seventh aspect of the center of gravity shifting training system relating to the present invention, in addition to the sixth aspect, the control device includes a center of gravity shifting estimation unit. The center of gravity shifting estimation unit is configured to perform estimation of center of gravity shifting of the user based on the operation history stored in the operation storage unit. The presentation unit is configured to present a result of the estimation by the center of gravity shifting estimation unit along with the operation history.

As for the eighth aspect of the center of gravity shifting training system relating to the present invention, in addition to the seventh aspect, the center of gravity shifting estimation unit is configured to estimate a following performance of the operation image with respect to the target image based on a target history indicating a history of the position of the target image and the operation history.

As for the ninth aspect of the center of gravity shifting training system relating to the present invention, in addition to the seventh or eighth aspect, the setting determination unit is configured to correct the setting data stored in the setting data storage unit according to a result of the estimation by the center of gravity shifting estimation unit.

As for the tenth aspect of the center of gravity shifting training system relating to the present invention, in addition to any one of the first to ninth aspects, a half mirror is disposed in front of the display screen. A thickness direction of the half mirror coincides with a normal direction of the display screen.

As for the eleventh aspect of the center of gravity shifting training system relating to the present invention, in addition to any one of the first to ninth aspects, the center of gravity shifting training system further include an image pickup device configured to shoot the user during the training period to create an image of the user. The display processing unit is configured to display a user image based on the image of the user created at the image pickup device on the display screen.

DESCRIPTION OF EMBODIMENTS

In the following embodiments, a center of gravity shifting training system for use in rehabilitation targeted for a patient whose center of gravity shifting function has deteriorated due to a disease and injury to enable the patient to perform a smooth center of gravity shifting. The description on the following embodiments, however, is not intended to limit the use of the center of gravity shifting training system, and the center of gravity shifting training system may be used for daily exercises of an able-bodied person and training for learning the feeling of center of gravity shifting necessary for various sports.

First Embodiment

Figure 1:
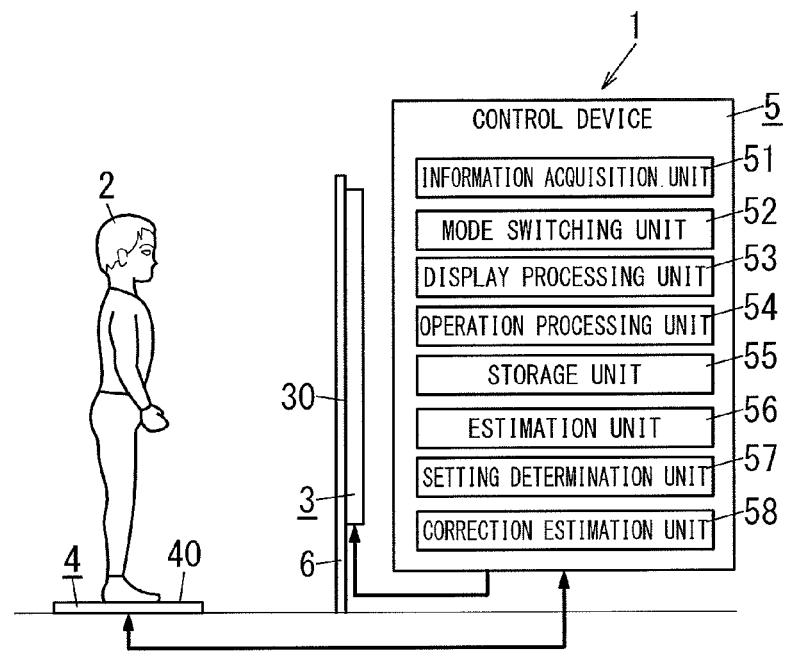
FIG. 1 is a schematic diagram illustrating the system configuration of a center of gravity shifting training system of the first embodiment.

The center of gravity shifting training system 1 of the present embodiment includes, as shown in FIG. 1, a display device 3 for reflecting a picture on a display screen 30 disposed in front of a user 2, a measurement device 4 for measuring the center of gravity position of the user 2 in a horizontal plane, and a control device 5 for controlling the operations of the display device 3 and the measurement device 4. The display device 3 and the measurement device 4 are both connected to the control device 5. In the present embodiment, the user 2 uses the center of gravity shifting training system 1 in a posture standing on the measurement device 4 (standing position).

Moreover, the center of gravity shifting training system 1 further includes a half mirror 6 which is disposed in front (the user 2 side) of the display screen 30 which faces the user 2 of the display device 3. The half mirror 6 is disposed to stand vertically between the display device 3 and the user 2 such that the front face (mirror surface) faces the user 2, and transmits a picture, which is displayed on the display device 3 in the back, to the user 2 side.

The display device 3 has the display screen 30 for displaying an image. The display device 3 is made up of a plasma display in this instance and is attached to the back face side of the half mirror 6. Although, in FIG. 1, illustrations of the structure for supporting the half mirror 6 and the attaching structure of the display device 3 is omitted, the half mirror 6 and the display device 3 are secured at a fixed position with a sufficient strength by an appropriately selected structure. Note that the display device 3 may be another displaying apparatus such as a liquid crystal display without being limited to the plasma display. Moreover, it is conceivable that in place of the displaying apparatus, a display device made up of a diffusion sheet (not shown) which is stuck on the back face of the half mirror 6, and a projection apparatus (not shown) which projects a picture onto the diffusion sheet from the backward of the half mirror 6 (the opposite side to the user 2) is used.

In the present embodiment, the half mirror 6 has a vertically oriented, rectangular front face and is formed into a size which functions as a looking glass which reflects a whole body of the user 2. The transmissivity of the half mirror 6 is designed such that the half mirror 6 can be used as a mirror, and besides the user 2 can view a picture displayed on the display device 3 through the half mirror 6. The half mirror 6 is formed by applying a mirror-surface coating by a metal film etc. to at least one surface of a transparent substrate of glass or plastic.

Here, the display device 3 is disposed such that the display screen 30 is in contact with the back face of the half mirror 6. The height position of the display device 3 is determined such that a lower end edge is positioned at a predetermined space apart from the lower end of the half mirror 6, and an upper end edge is positioned at a predetermined space apart from the upper end of the half mirror 6. Where, the display device 3 is disposed slightly upward from the center of the half mirror 6. Moreover, a transparent material which adjusts the refractive index to prevent reflection may be placed between the half mirror 6 and the display screen 30 such that a picture displayed on the display device 3 can be displayed at a high luminance on the front face of the half mirror 6.

According the above described configuration, the front face of the half mirror 6 functions to reflect a mirror image of the user 2 as a mirror and also to reflect a picture disposed on the display screen 30 of the display device 3. That is, when the user 2 stands in front of the half mirror 6, the mirror image of the user 2 is reflected on the front face of the half mirror 6, as well as the picture displayed on the display device 3 passes through the half mirror 6 to be reflected on the front face of the half mirror 6. Although details will be described later, the picture displayed on the display device 3 is produced by the control device 5.

The measurement device 4 is configured to have a working face which receives a load from the user 2 and to measure the center of gravity position of the user 2 in the working face. The measurement device 4 is disposed on the floor in front of the half mirror 6 and at the feet of the user 2. The measurement device 4 includes a boarding base 40 on which the user 2 boards, and a plurality of load sensors (not shown) for measuring loads acting to the boarding base 40 from the user 2 standing on the boarding base 40. In the present embodiment, the working face is the upper face of the boarding base 40. Not less than 3 load sensors are provided so as not to be aligned on a straight line in a horizontal plane, and are two-dimensionally disposed so as to be spaced apart as much as possible in the horizontal plane. For example, the boarding base 40 is formed into a rectangular shape. The measurement device 4 includes four load sensors. The four load sensors are disposed at positions respectively corresponding to the four corners of the boarding base 40. Note that the load sensor is, for example, a load cell. Moreover, the measurement device 4 includes a computing device (not shown) which calculates a center of gravity position from the loads measured by the four load sensors.

Using the measurement device 4 makes it possible to measure the center of gravity position in the horizontal plane of the user 2 standing on the boarding base 40 by evaluating the loads which respectively act on each load sensor. That is, when the body of the user 2 is not inclined in the fore and aft direction or the left and right direction, the proportion of load becomes equal in each of the fore and aft direction and the left and right direction, and the center of gravity position of the user 2 is located at the center of the boarding base 40.

The measurement device 4 measures the deviation of the load in real time for each of the fore and aft direction and the left and right direction with reference to the state in which the center of gravity position is located at the center of the boarding base 40, and evaluates the center of gravity position in the horizontal plane according to the deviation. In the present embodiment, the measurement device 4 evaluates a coordinate position of the center of gravity of the user 2 in a two-dimensional, orthogonal coordinate system in which the center position of the boarding base 40 is given as $(X, Y)=(0, 0)$, with the left and right direction of the user 2 in a state of facing the half mirror 6 being as the X axis and the fore and aft direction thereof being as the Y axis. Note that the right direction is the positive direction of the X axis, the left direction is the negative direction of the X axis, the fore direction is the positive direction of the Y axis, and the aft direction is the negative direction of the Y axis.

In this way, the measurement device 4 measures in real time the center of gravity position of the user 2 in a horizontal plane, and outputs the measured result (center of gravity position) to the control device 5. However, the measurement result of the measurement device 4 which is outputted to the control device 5 may be any value which can identify the center of gravity position of the user 2 in a horizontal plane, and the measurement device 4 may be configured to output, for example, the loads respectively acting on each load censor to the control device 5. In this instance, at the control device 5, the proportion of load is calculated for each of the fore and aft direction and the left and right direction by using the measured result of the measurement device 4, and the center of gravity position of the user 2 in a horizontal plane is calculated.

The control device 5 has two operation modes including a training mode and a setting mode. In the training mode, the control device 5 displays an operation image which is shifted according to the center of gravity position measured at the measurement device 4 and a target image indicating a destination of the operation image on the display screen 30. In the setting mode, the control device 5 prepares setting data indicating the position of the target image in the display screen 30.

Figure 2:
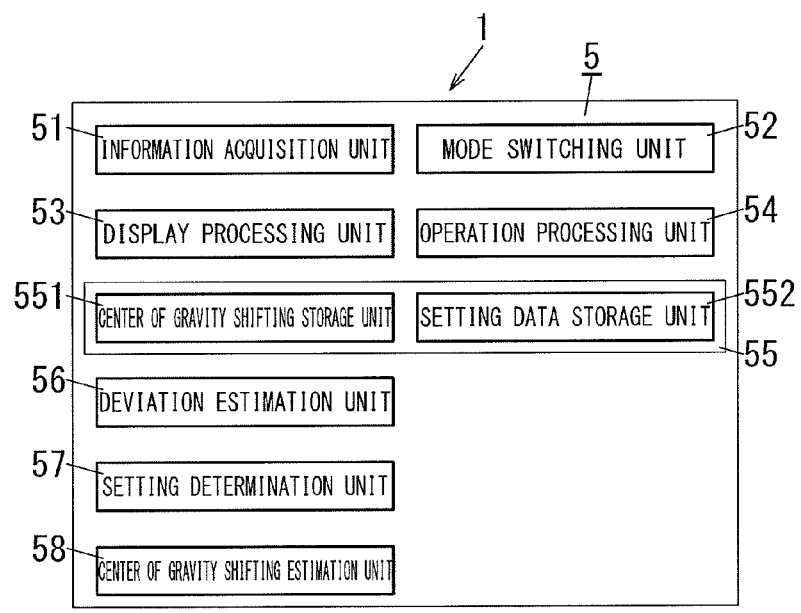
FIG. 2 is a schematic diagram illustrating a partially omitted system configuration of the center of gravity shifting training system of the first embodiment.

As shown in FIG. 2, the control device 5 includes an information acquisition unit 51, a mode switching unit 52, a display processing unit 53, an operation processing unit 54, a storage unit 55, an estimation unit (deviation estimation unit) 56, and a setting determination unit 57.

The mode switching unit 53 is configured to switch the operation mode of the control device 5 between the training mode and the setting mode.

The information acquisition unit 51 is configured to acquire a center of gravity position from the measurement device 4.

The storage unit 55 has a center of gravity position storage unit 551 configured to store the center of gravity position acquired by the information acquisition unit 51 in a setting period in which the operation mode of the control device 5 is the setting mode.

The deviation estimation unit 56 is configured to perform (make) estimation of the deviation of the center of gravity position based on the center of gravity position stored in the center of gravity position storage unit 551.

The setting determination unit 57 is configured to prepare the setting data indicating the position of the target image according to the result of the estimation by the deviation estimation unit 56. For example, the setting determination unit 57 is configured to create the setting data indicating the position of the target image according to the result of the estimation by the deviation estimation unit 56. In this instance, the setting determination unit 57 may correct the reference data prepared in advance according to the result of the estimation by the deviation estimation unit 56 and create the setting data indicating the position of the target image according to the result of estimation by the deviation estimation unit 56. Note that the setting determination unit 57 may select the setting data indicating the position of the target image according to the result of the estimation by the deviation estimation unit 56 from a plurality of the setting data prepared in advance.

The storage unit 55 has a setting data storage unit 552 configured to store the setting data prepared at the setting determination unit 57.

The operation processing unit 54 is configured to determine the display position of the operation image in the display screen 30 according to the center of gravity position acquired at the information acquisition unit 51.

Figure 3:
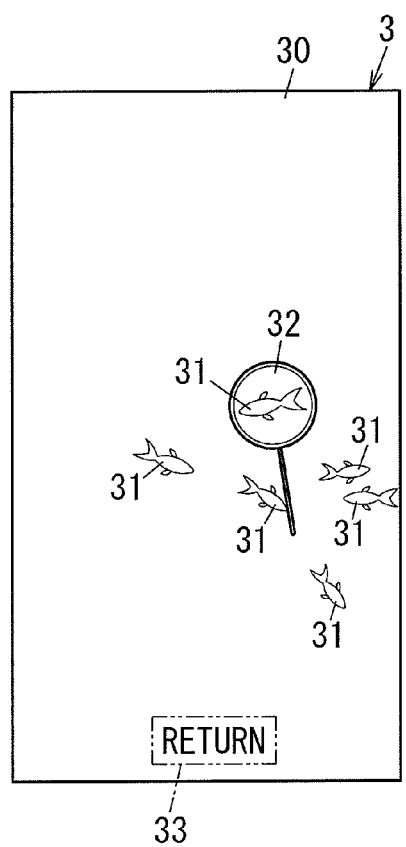
FIG. 3 is an explanatory diagram illustrating a display example of a display device of the center of gravity shifting training system of the first embodiment.
Figure 4:
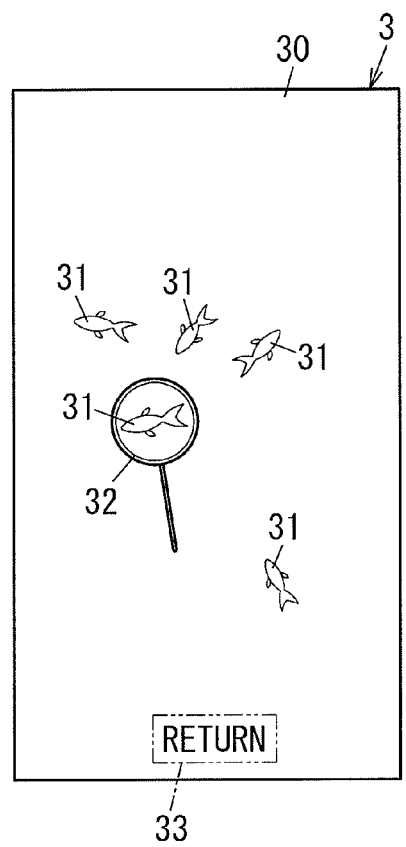
FIG. 4 is an explanatory diagram illustrating a display example of the display device of the center of gravity shifting training system of the first embodiment.

The display processing unit 53 is configured to display the operation image (operation icon) 32 at the display position determined at the operation processing unit 54 as shown in FIGS. 3 and 4 in a training period in which the operation mode of the control device 5 is the training mode, and display the target image (target icon) 31 on the display screen 30 based on the setting data stored in the setting data storage unit 552.

Further, the control device 5 includes a center of gravity shifting estimation unit (correction estimation unit) 58. The center of gravity shifting estimation unit 58 is configured to perform the estimation of the center of gravity shifting of the user 2 based on the position of the operation image in a training period. The setting determination unit 57 is configured to correct the setting data stored in the setting data storage unit 552 according to the result of the estimation by the center of gravity shifting estimation unit 58.

That is, in the center of gravity shifting training system 1 of the present embodiment, the control device 5 includes the information acquisition unit 51 configured to acquire the information of the center of gravity position from the measurement device 4 as the center of gravity information, and the mode switching unit 52 configured to switch the operation mode of the control device 5. Further, the control device 5 includes the display processing unit 53 configured to control the display device 3 to display the operation icon and the target icon, the operation processing unit 54 configured to vary the position of the operation icon in the display screen 30 based on the center of gravity position of the user 2, and the storage unit 55.

The mode switching unit 52 switches the two operation modes of the training mode and the setting mode upon a predetermined operation being performed on an input interface (not shown) of the control device 5. That is, as the result of the user 2 or a therapist etc. operating the input interface of the control device 5, the operation mode of the control device 5 is switched between the training mode and the setting mode. Although details will be described below, the training mode is an operation mode for allowing the user 2 to actually perform the center of gravity shifting training, and the setting mode is an operation mode for performing the setting etc. of the center of gravity shifting training which is to be performed by the user 2 in the training mode.

The display processing unit 53 displays the operation icon 32 and the target icon 31 on the display screen 30 at the same time in the training mode. That is, in the training period, the display processing unit 53 controls the display device 3 in such a manner to display the operation icon (operation image) 32 and the target icon (target image) 31 on the display screen 30. The operation icon 32 and the target icon 31 as referred to herein are both icons which occupy a sufficiently small area on the display screen 30 compared to the total area of the display screen 30, and are movably displayed in the display screen 30. In the present embodiment, an image representing a goldfish is employed as the target icon 31 as exemplified in FIGS. 3 and 4, and an image representing a poi (scooping net) for scooping a goldfish is employed as the operation icon 32. While 6 goldfish images are displayed on the display screen 30 in the example of FIG. 3, each of those goldfish images is the target icon 31. The target icon 31 is not a stationary image of goldfish, but is made up of a moving image of goldfish which swings as if swimming in the water.

The operation processing unit 54 varies the display position of the operation icon 32 in the display screen 30 based on the center of gravity position of the user 2 in a horizontal plane which is measured at the measurement device 4 in the training mode. Specifically, the operation processing unit 54 regards a position which is evaluated by transforming the coordinate position (X, Y) of the center of gravity of the user 2 acquired at the information acquisition unit 51 into a position on the display screen 30 as the position of the operation icon 32. The operation processing unit 54 acquires the center of gravity information from the information acquisition unit 51 on a predetermined cycle (for example, 1/30 sec) to determine the position of the operation icon 32 such that the center of gravity position of the user 2 is reflected in substantially real time to the position of the operation icon 32 on the display screen 30.

Here, the operation processing unit 54 performs coordinate transformation such that the left and right of the user 2 corresponds to the left and right of the display screen 30, the forward of the user 2 to the upward of the display screen 30, and the rearward of the user 2 to the downward of the display screen 30. For that reason, when for example the user 2 leans its body to the right side to shift the center of gravity position to the right, the operation icon 32 on the display screen 30 is shifted to the right in accordance with the center of gravity shifting, and when the user 2 leans its body forward to shift the center of gravity position forward, the operation icon 32 on the display screen 30 is shifted upward. Further, the shifting velocity and acceleration etc. of the center of gravity position of the user 2 are also reflected to the shifting of the operation icon 32.

The target icon 31 is an icon which provides a target for the following by the operation icon 32. While the target icon 31 may be an icon which is displayed at a fixed position on the display screen 30, the display processing unit 53 controls the display device 3 in such a manner to display the target icon 31 in the present embodiment such that the target icon 31 is shifted in the display screen 30. As a result of this, while the control device 5 is operating in the training mode, the user 2 can follow (track) the target icon 31 which moves around on the display screen 30 with the operation icon 32 by operating the operation icon 32 on the display screen 30 through the center of gravity shifting of its own.

Here, the storage unit 55 (setting data storage unit 552) stores image data (image data of goldfish and poi in the present embodiment) representing the contents of the operation icon 32 and the target icon 31, and the setting data for determining the position and movement of the target icon 31 on the display screen 30. The shifting pattern of the target icon 31 includes a pattern of randomly moving around, and a pattern having a certain regularity, and the setting data also determines which pattern the display processing unit 53 selects. Further, the setting data includes data for determining the number, shifting velocity, and acceleration etc. of the target icon 31.

The operation icon 32 and the target icon 31 are associated with the relevant processing such that respective predetermined processing is performed when the positions thereof on the display screen 30 overlap with each other. That is, by associating the processing to be performed with the operation icon 32 and the target icon 31 respectively, the display processing unit 53 can cause the processing associated with each icon to be performed when the positions of the operation icon 32 and the target icon 31 overlap.

To be specific, the target icon 31 is associated with a processing whereby a graphic of goldfish disappears with an animation that a goldfish is scooped with a poi in the operation icon 32 when the position of the target icon 31 overlaps that of the operation icon 32. Further, the operation icon 32 is associated with a processing to perform an animation to scoop a goldfish in the target icon 31 with the poi when the position of the operation icon 32 overlaps that of the target icon 31.

That is, every time the user 2 scoops a goldfish of the target icon 31 by operating the operation icon 32, the number of goldfishes (target icons 31) to be displayed is kept on decreasing while the control device 5 is in operation (that is, in a training period) in the training mode. For example, if the user 2 scoops a goldfish in a state in which 6 goldfishes are displayed as in FIG. 3, the number of the goldfishes will become 5 as shown in FIG. 4. Further, the operation icon 32 may be associated with a processing whereby a sound corresponding to a change of the graphic, such as a sound of splashing water when scooping a goldfish is generated from a speaker (not shown) of the control device 5 when the position of the operation icon 32 overlaps that of the target icon 31.

Here, the display processing unit 53 judges that the positions of both the icons have overlapped when a representative point of the operation icon 32 is located within a determination region which is set in a predetermined range from the coordinate position of a representative point of the target icon 31 (for example, the center point of the target icon 31). However, the display processing unit 53 does not judge that both the icons have overlapped immediately after the representative point of the operation icon 32 enters into the determination region, but judges that both the icons have overlapped only after a predetermined time which is measured by a timer (not shown) has passed in a state in which the representative point of the operation icon 32 is located in the determination region.

As a result of this, the user 2 can scoop a goldfish of the target icon 31 only when the user 2 operates the operation icon 32 such that it slowly approaches the target icon 31. Further, the operation icon 32 may be associated with a processing whereby the poi is broken when the representative point of the operation icon 32 (for example, the center point of the operation icon 32) has passed through the determination region, that is, when the poi in the operation icon 32 has passed through the goldfish in the target icon 31.

In this situation, the training mode in which the display processing unit 53 causes the display device 3 to display the target icon 31 and the operation icon 32 thereby allowing the user 2 to perform the center of gravity shifting training is started by performing a predetermined operation to start the training on the input interface of the control device 5 as described above. That is, as the result of the operation mode of the control device 5 being switched from the setting mode to the training mode by the mode switching unit 52, the center of gravity shifting training of the user 2 is started. This training mode may be ended at the time when all the goldfishes displayed are scooped, or a predetermined time limit has passed from the start of the training, or may be ended by performing a predetermined operation to end the training on the input interface of the control device 5 without providing a time limit.

The display processing unit 53 causes the display device 3 to display the number of goldfishes scooped by the user 2 within a time limit, the time needed to scoop all the goldfishes displayed, and the like as scores when the training mode is ended. That is, the result of the center of gravity shifting training which is performed by the user 2 in the training mode is displayed on the display device 3 when the mode switching unit 52 ends the training mode and switches it to the setting mode. Note that in the example of FIGS. 3 and 4, the control device 5 compulsorily ends the training mode as the result of the operation icon 32 being overlapped on a return button 33 displayed in the lower portion of the display screen 30 for not less than a predetermined time.

Using the above described center of gravity shifting training system 1 allows the user 2 to operate the operation icon 32 on the display screen 30 by performing center of gravity shifting and to scoop a goldfish in the target icon 31 with a poi in the operation icon 32 while viewing the mirror image of its own reflected on the half mirror 6 in the training mode. At this moment, the user 2 will perform the center of gravity shifting in accordance with the movement of the target icon 31 so as to appropriately catch the target icon 31 which moves around on the display screen 30 with the operation icon 32. Therefore, since as a result of aiming at a high score, the user 2 will move the center of gravity of its body without particular consciousness, the user 2 can enjoy sufficient effects of the center of gravity shifting training by moving the body with a feeling of enjoying games.

By the way, in the center of gravity shifting training system 1, the position and movement of the target icon 31 on the display screen 30 in the training mode is determined by the setting data stored in the storage unit 55 (the setting data storage unit 552). However, when the center of gravity shifting training system 1 is targeted for an unspecified large number of users 2, or the like, it is difficult for the user 2 or a therapist etc. to create setting data respectively suitable for each user 2, or to select setting data among a plurality of setting data.

Accordingly, in the center of gravity shifting training system 1 of the present embodiment, the control device 5 further includes an estimation unit (deviation estimation unit) 56 configured to estimate the center of gravity information appropriately acquired at the information acquisition unit 51 in the setting mode, and a setting determination unit 57 configured to automatically determine the setting data based on the estimation result at the estimation unit 56.

That is, in the setting mode, the storage unit 55 (center of gravity position storage unit 551) stores center of gravity information appropriately acquired at the information acquisition unit 51, and the estimation unit 56 estimates the deviation of the center of gravity position of the user 2 by using the center of gravity information stored in the storage unit 55 (center of gravity position storage unit 551) during the setting mode. The estimation result is inputted to the setting determination unit 57 and used for the determination of the setting data. The setting determination unit 57 determines the setting data for determining the position and movement of the target icon 31 on the display screen 30 in the training mode, based on the estimation result (deviation of center of gravity position) at the estimation unit 56 in the setting mode before the training mode is started, and stores it in the storage unit 55 (setting data storage unit 552).

To be specific, in the setting mode, in order to provide the center of gravity information which becomes an estimation target at the estimation unit 56 to the information acquisition unit 51, a therapist etc. gives instruction to the user 2 to freely shift the center of gravity in the fore and aft, and the left and right directions in a state of standing on the boarding base 40. Here, the information acquisition unit 51 acquires center of gravity information at a predetermined cycle (for example, ⅓₀ sec) and stores it in a time series in the storage unit 55 (center of gravity position storage unit 551). For example, in the present embodiment, the information acquisition unit 51 acquires a center of gravity position from the measurement device 4 at a predetermined time interval (for example, 100 msec). Therefore, the center of gravity position storage unit 551 stores the center of gravity position (X, Y) for each of the predetermined time interval. Note that an instruction to estimate the center of gravity position may be stored in the storage unit 51 in advance. In this instance, the control device 5 causes an instruction to perform the estimation of center of gravity position to be displayed on the display screen 30 in the training period.

Figure 5:
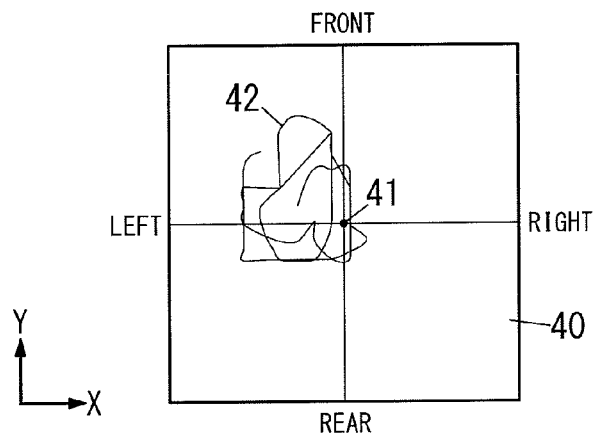
FIG. 5 is an explanatory diagram of the operation of the center of gravity shifting training system of the first embodiment.

This will result in that in the setting mode, a track of the center of gravity position when the user 2 freely leans its body to the fore and aft, and the left and right within a possible range, to shift the center of gravity will be stored in the storage unit 55 (center of gravity position storage unit 551). The track of the center of gravity position reflects the function and habit of center of gravity shifting of the user 2. For example, in the case of a user 2 who is weak at center of gravity shifting to rightward and rearward, the track of center of gravity position obtained in the setting mode will become a track 42 which is deviated to the left and forward with respect to the center position 41 of the boarding base 40 as shown in FIG. 5. FIG. 5 schematically shows the track 42 of the center of gravity position on the upper face of the boarding base 40. When such a center of gravity position is obtained in the setting mode, the estimation unit 56 estimates that the center of gravity position of the user 2 is deviated to the left and forward, in other words, estimates that the user 2 is weak at center of gravity shifting to rightward and rearward.

For example, the deviation estimation unit 56 produces an image (distribution image) indicating the distribution of center of gravity position based on the center of gravity position stored in the center of gravity position storage unit 551. The distribution image is an image (image of 40×40) made up of a region (pixel) which partitions each of the X and Y axes into a range of 5% of a maximum value. The pixel value of the distribution image indicates the number of times at which the center of gravity is located at a corresponding region. For example, when the maximum value of the X axis is 200 and the maximum value of the Y axis is 200, a center of gravity position (28, −84) indicates (14%, −42%). Since this center of gravity position is included in the region where X is not less than 10% and less than 15%, and Y is not less than −45% and less than −40%, the pixel value of this region is added by 1. By repeating such computation, the deviation estimation unit 56 produces a distribution image. Next, the deviation estimation unit 56 smoothes the distribution image by using a smoothing filter (moving average filter). For example, a 3×3 smoothing filter is used. Thereafter, the deviation estimation unit 56 compares the pixel value of the distribution image with a predetermined threshold value, and estimates that there is a deviation in the center of gravity position if the pixel value is not less than the predetermined threshold value. That is, the deviation estimation unit 56 binarizes the distribution image and produces an estimation image which is a binary image indicating the presence or absence of the deviation of center of gravity position for each region. In this estimation image, the pixel value of a region (pixel) where there is a deviation in the center of gravity position is "1 (corresponding to black color)" and the pixel value of a region where there is no deviation in the center of gravity position is "0 (corresponding to white color)." The above described predetermined threshold value is a relatively low value. Note that the above described predetermined threshold value may be 0. A binary image thus obtained indicates a region where the center of gravity is located on the upper face of the boarding base 40.

Based on the estimation result (deviation of center of gravity position), the setting determination unit 57 determines the setting data for determining the position and movement of the target icon 31 so as to make the user 2 perform the center of gravity shifting predominantly in the direction in which the user 2 is presumed to be weak at. In short, when the track 42 as shown in FIG. 5 is obtained in the setting mode, the setting determination unit 57 determines the setting data such that the target icon 31 is displayed to be deviated rightward or downward in the display screen 30 in the training mode. At this moment, the setting determination unit 57 may determine the setting data by correcting the fundamental data stored in the storage unit 55 (setting data storage unit 552) in advance based on an estimation result, or select one piece of setting data from a plurality of candidates of the setting data stored in the storage unit 55 (setting data storage unit 552) in advance.

For example, the setting determination unit 57 creates setting data which causes the target icon 31 to randomly appear in a region having a predetermined size and centering on a predetermined reference point. In this instance, the setting determination unit 57 selects the above described predetermined reference point from regions where the pixel value is 0 (region where there is no deviation of the center of gravity position) in an estimation image produced at the deviation estimation unit 56. Note that as preprocessing for selecting the predetermined reference point, the setting determination unit 57 may perform processing to decrease the number of pixels of an estimation image. For example, the setting determination unit 57 transforms an estimation image of 20×20 into an estimation image of 4×4, 5×5, or 6×6.

As another example, the setting determination unit 57 may create setting data which causes the target icon 31 to randomly appear in a region in the periphery of a predetermined reference line. In this instance, the setting determination unit 57 detects a place where regions whose pixel value is "0" gather from an estimation image and selects a line surrounding the detected place as the predetermined reference line. Alternatively, the setting determination unit 57 detects a place where regions whose pixel value is "1" gather from an estimation image and selects a line surrounding the detected place as the predetermined reference line.

Further, the setting determination unit 57 may create setting data such that the target icon 31 is shifted on the display screen 30. In this instance, the target icon 31 may be shifted randomly. Moreover, the target image 31 may be shifted along a line surrounding a place where regions whose pixel value is "1" gather. Alternatively, the target image 31 may appear inside a region whose pixel value is "1", and thereafter be shifted to outside the concerned region.

Note that the estimation image is a binary image in the above described example. However, the estimation image may be a gray image.

In this instance, the setting determination unit 57 may create setting data which causes the target icon 31 to appear at a predetermined appearance probability for each predetermined region on the display screen 30. Here, the appearance probability of the target icon 31 is determined based on the pixel value of the estimation image. For example, the appearance probability is determined so as to be proportional to the inverse of the pixel value of the estimation image. Further, in this instance as well, the target icon 31 may be shifted on the display screen 30. For example, the target icon 31 may be shifted from a location of a larger pixel value of the estimation image to a location of a smaller pixel value thereof.

Moreover, even when the estimation image is a gray image, the setting determination unit 57 may create setting data which causes the target icon 31 to appear in a region having a predetermined size and centering on a predetermined reference point. As a preprocessing to select the predetermined reference point, the setting determination unit 57 performs processing to decrease the number of pixels of the estimation image. For example, the setting determination unit 57 transforms an estimation image of 20×20 into an estimation image of 4×4, 5×5, or 6×6. After performing the processing to decrease the number of pixels of the estimation image, the setting determination unit 57 selects a region, whose pixel value is not more than a first predetermined value and whose distance from the center is not more than a second predetermined value, as the predetermined reference point from the estimation image. Ideally, the setting determination unit 57 selects a region, whose pixel value is lowest and which is closest to the center, as the predetermined reference point.

Alternatively, the setting determination unit 57 may determine the setting data so as to refrain center of gravity shifting in the direction in which the user 2 is presumed to be weak at based on the deviation of the center of gravity position of the user 2 estimated at the estimation unit 56. In this instance, the user 2 will not be compelled to perform unnatural center of gravity shifting, thereby avoiding the user 2 from being subjected to an excessive load.

Moreover, the estimation unit 56 may estimate a shifting velocity of the center of gravity and an extent of shifting range the center of gravity of the user 2, and in this instance, the setting determination unit 57 may determine the setting data such that the shifting velocity and shifting range of the target icon 31 are limited according to the estimation result of the estimation unit 56. Besides, the setting determination unit 57 may determine the setting data such that the level of difficulty of shifting pattern of the target icon 31 (the number and acceleration etc. of the target icon 31) is determined according to the estimation result of the estimation unit 56.

Further, the display processing unit 53 may be configured to cause the display device 3 to display the center of gravity information to be used for the estimation at the estimation unit 56 in the setting mode. That is, the display processing unit 53 may be configured to display the center of gravity position stored in the center of gravity position storage unit 551 on the display screen 30 in the setting period. In this instance, the display processing unit 53 displays an icon at a position which is evaluated by transforming the coordinate position of a center of gravity into a position on the display screen 30, or display a track of center of gravity position as shown in FIG. 5 on the display screen 30 in the setting mode.

As a result of this, the user 2 can perform center of gravity shifting while confirming the center of gravity information displayed on the display device 3 in the setting mode, and becomes able to shift its center of gravity uniformly within a possible range. Therefore, the user 2 can avoid a situation in which the track of the center of gravity position is deviated leftward even when the user 2 is not particularly weak at center of gravity shifting to rightward, so that the accuracy of estimation at the estimation unit 56 will be improved.

In this way, in the present embodiment, the setting mode is determined based on the estimation result of the center of gravity information when the user 2 freely performs center of gravity shifting, in the setting mode before the training mode, and the determined setting mode is to be stored in the storage unit 55 (setting mode storage unit 552). After the operation mode of the control device 5 is switched to the training mode, the display processing unit 53 causes the target icon 31 to be displayed on the display screen 30 by using the setting data stored in the storage unit 55 (setting mode storage unit 552) so that the target icon 31 is displayed according to the setting data determined at the setting determination unit 57.

Moreover, in the present embodiment, the control device 5 further includes a correction estimation unit 58 for estimating the movement of the operation icon 32 displayed on the display screen 30 in the training mode, and the setting determination unit 57 corrects the setting data as needed based on the estimation result of the correction estimation unit 58 during operation in the training mode. For example, the correction estimation unit (center of gravity shifting estimation unit) 58 is configured to perform the estimation of the center of gravity shifting of the user 2 based on the position of the operation image 32 in the training period, and the setting determination unit 57 is configured to correct the setting data stored in the setting data storage unit 552 according to the result of estimation by the center of gravity shifting estimation unit 58. That is, although the setting determination unit 57 predetermines the setting data for determining the position and movement of the target icon 31 at the starting point of the training mode, in the setting mode, it can correct the setting data as needed during the training mode according to the movement of the user 2 after the start of the training mode. Note that, the correction estimation unit 58 estimates the movement of the operation icon 32 at a fixed time interval during the training mode.

In the present embodiment, the correction estimation unit 58 is configured to create an estimation image as with the estimation unit 56. That is, the correction estimation unit 58 is configured to create the estimation image based on the center of gravity position acquired by the information acquisition unit 51 in a predetermined period during the training period. In other words, the correction estimation unit 58 is configured to perform the estimation of the deviation of the center of gravity position as the estimation of center of gravity shifting of the user 2. The setting determination unit 57 creates the setting data in the same manner as described above based on the estimation image created at the correction estimation unit 58.

For that reason, according to the correction estimation unit 58 and the setting determination unit 57, the setting data is corrected for each predetermined period during the training period. Therefore, after the setting data is prepared in the setting mode, the setting data is corrected for each predetermined period in the training mode.

Here, the function of the correction estimation unit 58 will be described taking as an example a case in which since a track 42 as shown in FIG. 5 is obtained in the setting mode, the setting determination unit 57 determines the setting data such that the target icon 31 is displayed as being deviated to rightward or downward of the display screen 30 in the setting mode.

In this instance, if the operation icon 32 is hardly able to follow (pursue) the rightward and downward movement of the target icon 31 in the training mode, the correction estimation unit 58 estimates that center of gravity shifting to rightward and rearward is not achieved. Responding to this estimation result, the setting determination unit 57 corrects the setting data such that the shifting of the target icon 31 to rightward and downward is reduced, or the shifting velocity and shifting range of the target icon 31 are limited, or the level of difficulty of the shifting pattern of the target icon 31 is reduced. As a result of that, the user 2 becomes able to follow the target icon 31 with the operation icon 32 without performing undue center of gravity shifting, and it is possible to avoid the user 2 from being subjected to an excessive load.

On the other hand, if the operation icon 32 is adequately able to chase the rightward and downward movement of the target icon 31 in the training mode, the correction estimation unit 58 estimates that center of gravity shifting to rightward and rearward is achieved. Responding to this estimation result, the setting determination unit 57 corrects the setting data such that the shifting of the target icon 31 to rightward and downward is increased, or the limits of the shifting velocity and shifting range of the target icon 31 are relaxed, or the level of difficulty of the shifting pattern of the target icon 31 is raised. As a result of that, the level of difficulty of the center of gravity shifting training is raised in accordance with the degree of recovery (or the degree of growth) of the function of center of gravity shifting of the user 2 so that the efficiency of the center of gravity shifting training will be improved.

Further, when the center of gravity shifting training system 1 is alternately used by a plurality of specified users 2, the storage unit 55 (setting data storage unit 552) may have a storage region for storing setting data for each user 2. As a result of this, when a user 2 for whom the setting data has already been determined (or corrected) at the setting determination unit 57 performs training again, the control device 5 also becomes able to start the training mode skipping the setting mode by reading out the setting data for the user 2 from the storage unit 55 (setting data storage unit 552).

As so far described, a center of gravity shifting training system 1 of the present embodiment includes the display device 3, the measurement device 4, and the control device 5. The display device 3 is configured to display a picture on the display screen 30. The measurement device 4 is configured to measure the center of gravity position in the horizontal plane of the user 2 facing the display screen 30. The control device 5 is configured to control the operations of the display device 3 and the measurement device 4. The control device 5 includes the information acquisition unit 51, the mode switching unit 52, the display processing unit 53, the operation processing unit 54, the storage unit 55, the estimation unit 56, and the setting determination unit 57. The information acquisition unit 51 is configured to acquire the information of the center of gravity position measured at the measurement device 4 as the center of gravity information. The mode switching unit 52 is configured to switch the two operation modes of the training mode and the setting mode. The display processing unit 53 is configured to control the display device 3 to display the operation icon 32 and the target icon 31 which is the target for the following by the concerned operation icon 32 in the training mode. The operation processing unit 54 is configured to vary the position of the operation icon 32 in the display screen 30 according to the center of gravity information in the training mode. The storage unit 55 is configured to store the center of gravity information. The estimation unit 56 is configured to estimate the deviation of the center of gravity position of the user 2 from the center of gravity information stored in the storage unit 55 in the setting mode. The setting determination unit 57 is configured to determine the setting data which determines the position of the target icon 31 on the display screen 30 in the training mode based on the deviation of the center of gravity position estimated at the estimation unit 56.

In other words, the center of gravity shifting training system 1 of the present embodiment includes the display device 3, the measurement device 4, and the control device 5. The display device 3 has a display screen 30 for displaying an image. The measurement device 4 has the base (boarding base) 40 having the working face for receiving a load from the user 2 and is configured to measure the center of gravity position of the user 2 in the working face. The control device 5 has two operation modes including the training mode and the setting mode. The control device 5 is configured to, in the training mode, display the operation image 32 which is shifted according to the center of gravity position measured at the measurement device 4, and the target image 31 which indicates the destination of the operation image 32, on the display screen 30. The control device 5 is configured to, in the setting mode, prepare setting data which indicates the position of the target image 31 in the display screen 30. The control device 5 includes the mode switching unit 52, the information acquisition unit 51, the center of gravity position storage unit 551, the deviation estimation unit 56, the setting determination unit 57, the setting data storage unit 552, the operation processing unit 54, and the display processing unit 53. The mode switching unit 53 is configured to switch the operation mode of the control device 5 between the training mode and the setting mode. The information acquisition unit 51 is configured to acquire the center of gravity position from the measurement device 4. The center of gravity position storage unit 551 is configured to store the center of gravity position acquired by the information acquisition unit 51 in the setting period in which the operation mode of the control device 5 is the setting mode. The deviation estimation unit 56 is configured to make the estimation of the deviation of the center of gravity position based on the center of gravity position stored in the center of gravity position storage unit 551. The setting determination unit 57 is configured to prepare the setting data which indicates the position of the target image according to the result of estimation by the deviation estimation unit 56. The setting data storage unit 552 is configured to store the setting data prepared at the setting determination unit 57. The operation processing unit 54 is configured to determine the display position of the operation image in the display screen 30 according to the center of gravity position acquired at the information acquisition unit 51. The display processing unit 53 is configured to display the operation image (operation icon) 32 at the display position determined at the operation processing unit 54 as shown in FIGS. 3 and 4 in a training period in which the operation mode of the control device 5 is the training mode, and display the target image (target icon) 31 on the display screen 30 based on the setting data stored in the setting data storage unit 552.

According to the center of gravity shifting training system 1 of the present embodiment described so far, since the position of the target image 31 on the display screen 30 in the training mode is determined based on the deviation of the center of gravity position obtained in the setting mode before the training mode, it is possible to perform the center of gravity shifting training suitable for each user 2. That is, the center of gravity shifting training system 1 estimates the function and habits (for example, direction that the user is weak at) of center of gravity shifting of a user 2 before actually starting training, and automatically determines the position of the target icon 31 in the training mode based on the estimation result.

Therefore, the center of gravity shifting training system 1 can set the position of the target icon 31 suitable for each individual user 2 even when an unspecified large number of users 2 are targeted, and individually strengthen a movement which the user 2 is weak at for each user 2. As a result, the user 2 is allowed to perform individual center of gravity shifting training suitable for each user 2, and there is an advantageous effect in that the efficiency of the training is improved compared with a case where all of the users 2 who have similar symptoms are made to perform a rigidly uniform center of gravity shifting training.

Moreover, in the center of gravity shifting training system 1 of the present embodiment, the control device 5 further includes the correction estimation unit 58 for estimating the movement of the operation icon 32 in the display screen 30 in the training mode. The setting determination unit 57 is configured to correct the setting data based on the estimation result at the correction estimation unit 58 in the training mode.

In other words, the control device 5 includes the center of gravity shifting estimation unit (correction estimation unit) 58. The center of gravity shifting estimation unit 58 is configured to perform the estimation of the center of gravity shifting of the user 2 based on the position of the operation image 32 in the training period. The setting determination unit 57 is configured to correct the setting data stored in the setting data storage unit 552 according to the result of estimation by the center of gravity shifting estimation unit 58.

According to the center of gravity shifting training system 1 of the present embodiment, since the setting determination unit 57 corrects the setting data as needed based on the estimation result of the correction estimation unit 58 during operation in the training mode, it is possible to correct the position and movement of the target icon 31 such that the training is more suitable for the user 2 even while the user 2 is performing training. Therefore, it is possible to avoid the user 2 from being subjected to an excessive load, and to improve the efficiency of the center of gravity shifting training.

Moreover, the center of gravity shifting training system 1 of the present embodiment further includes a half mirror 6 which is disposed on the user 2 side with respect to the display screen 30, and which transmits a picture displayed on the display screen 30 and also reflects a mirror image of the user 2.

In other words, in the center of gravity shifting training system 1 of the present embodiment, the half mirror 6 is disposed in front of the display screen 30. The thickness direction of the half mirror 6 is in coincidence with the normal direction of the display screen 30.

According to the center of gravity shifting training system 1 of the present embodiment, since the user 2 can move while viewing its own mirror image reflected on the half mirror 6, the user 2 can visually learn how its center of gravity is shifted depending on various postures that it adopts. For that reason, there is an advantage that the user 2 can learn its body movement necessary for center of gravity shifting, such as how to lean its body when, for example, applying load on the right leg, while performing training.

That is, the user 2 can perform center of gravity shifting training while constantly confirming the posture of its own, and can perform center of gravity shifting while confirming a proper posture. For example, the user 2 can perform training to shift the center of gravity while confirming the inclination of its body. Particularly, the user 2 can perform center of gravity shifting while confirming that the positions of the left and right shoulders are horizontal by means of its own mirror image reflected on the half mirror 6. That is, the user 2 can perform training to shift its center of gravity while keeping the line connecting both the shoulders horizontal (while keeping the trunk straight). In this instance, the user 2 becomes able to perform center of gravity shifting while holding the left and right shoulders horizontal thereby keeping a proper posture, without trying to shift the body weight randomly so as to be able to shift the center of gravity consequently. Performing center of gravity shifting while confirming its own posture in this way is especially useful for a patient who has difficulty even in standing straight.

Here, even a configuration in which an image pickup device (not shown) for picking up an image of a user 2 from its front is provided, and a picture of a whole body of the user 2 taken by the image pickup device is left-right inverted by the control device 5 so that the inverted picture is displayed on the display device 3 makes it possible to allow the user 2 to see the whole body image of its own. Thus, in this instance as well, the same effect as that when the half mirror 6 is used can be obtained. However, it is difficult for the picture displayed by the display device 3 to perfectly reflect the movement etc. of the user 2 in real time due to factors such as time delay, image resolution, the illumination state of the object, deviation from the viewpoint of the user 2 due to the difference in the position of the image pickup device, and focal distance of the lens. For that reason, when the user 2 is shown only an inverted picture displayed on the display device 3 without providing the half mirror 6, the user 2 may have an uncomfortable feeling to some extent.

In contrast to this, the half mirror 6 is provided in the present embodiment, and the mirror image reflected on the front face of the half mirror 6 can substantially perfectly represent the movement etc. of the user 2 in real time since it reflects the figure of the user 2 in an optically faithful manner.

Furthermore, the user 2 can focus on either of the mirror image reflected on the half mirror 6 and the picture displayed on the display device 3 by switching the focal distance of the eye (the focal distance of picture:focal distance of mirror image=1:2). Accordingly, the user 2 can use the center of gravity shifting training system 1 while keeping its eyes on the picture (the target icon 31 and the operation icon 32) displayed on the display device 3 with the mirror image being in the field of view as well.

Moreover, it is desirable that the luminance of the display device 3 and the brightness in the room are appropriately adjusted during the usage of the center of gravity shifting training system 1 such that there is no significant difference in the appearance seen from the user 2 between the mirror image reflected on the half mirror 6 and the picture displayed on the display device 3.

Note that although an example of training supposing goldfish scooping with the target icon 31 being a goldfish and the operation icon 32 being a poi has been shown in the present embodiment, these icons are merely an example and, for example, the target icon 31 may be a fly and the operation icon 32 may be a fly swatter.

Moreover, the operation processing unit 54 may be configured to vary the position of the operation icon 32 in the display screen 30 based on the center of gravity position measured at the measurement device 4, and is not limited to the configuration in which the operation icon 32 is displayed at the position evaluated by coordinate transformation as described above. For example, the operation processing unit 54 may vary the position of the operation icon 32 according to the relative positional relationship between the center of the boarding base 40 and the center of gravity position. That is, when the user 2 leans its body to the right side and the center of gravity position deviates from the center of the boarding base 40 to the right, the operation processing unit 54 may be configured to shift the operation icon 32 in the display screen 30 to the right at an acceleration, for example, according to the deviation amount of the center of gravity position from the center position of the boarding base 40.

Second Embodiment

Figure 6:
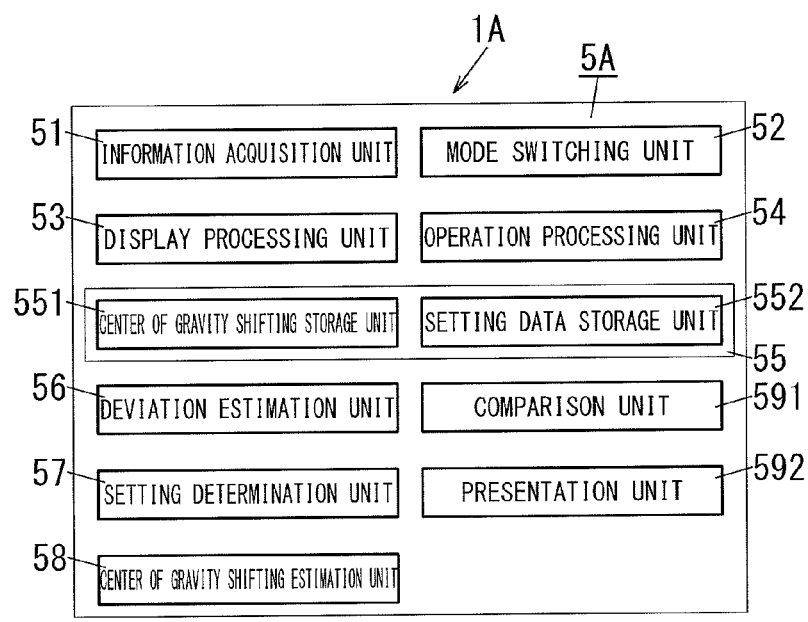
FIG. 6 is a schematic diagram illustrating a partially omitted system configuration of a center of gravity shifting training system of the second embodiment.

The center of gravity shifting training system 1A of the present embodiment differs from the center of gravity shifting training system 1 of the first embodiment in that the control device 5A includes a comparison unit 591 configured to compare the estimation result at the estimation unit 56 in the setting mode before and after the training mode; and a presentation unit 592 configured to present the comparison result at the comparison unit 591, as shown in FIG. 6.

That is, the center of gravity shifting training system 1A of the present embodiment includes the display device 3, the measurement device 4, the control device 5A, and the half mirror 6. Note that the display device 3, the measurement device 4, and the half mirror 6 are omitted in FIG. 6.

The control device 5A includes the mode switching unit 52, the information acquisition unit 51, the center of gravity position storage unit 551, the deviation estimation unit 56, the setting determination unit 57, the setting data storage unit 552, the operation processing unit 54, the display processing unit 53, and the center of gravity shifting estimation unit 58 as well as the comparison unit 591 and the presentation unit (comparison result presentation unit) 592.

In the present embodiment, the mode switching unit 52 switches the operation mode of the control device 5A from the setting mode to the training mode, and thereafter again switches to the setting mode again when the training mode ends. In the setting mode, to give the center of gravity information which becomes the object of estimation at the estimation unit 56 to the information acquisition unit 51 as described in the first embodiment, a therapist etc. gives an instruction to the user 2 to freely shift the center of gravity in the fore and aft, and the left and right in a state of standing on the mounting base 40. For that reason, in the setting mode, the track of the center of gravity position when the user 2 freely leans its body to the fore and aft, and the left and right directions to shift its center of gravity within a possible range will be stored in the storage unit 55. The estimation unit 56 estimates the center of gravity information obtained during operation in the setting mode not only in the setting mode before the training mode, but also in the setting mode after the training mode.

Figure 7:
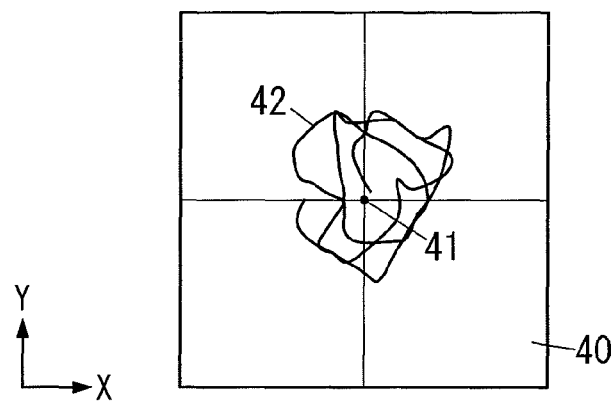
FIG. 7 is an explanatory diagram of the operation of the center of gravity shifting training system of the second embodiment.

For example, in the setting mode before the training mode, when a track (track) 42 of center of gravity position which is deviated to the left and forward with respect to the center position 41 of the boarding base 40 is obtained as shown in FIG. 5, the estimation unit 56 estimates that the center of gravity shifting of the user 2 is deviated to the left and forward. In contrast to this, in the setting mode after the training mode, when the track 42 of center of gravity position in which there is no large deviation with respect to the center position 41 of the boarding base 40 is obtained as shown in FIG. 7, the estimation unit 56 estimates that the center of gravity shifting is balanced. FIG. 7 schematically shows the track 42 of the center of gravity position in the upper face of the boarding base 40. Moreover, the estimation unit 56 may perform estimation to numerically determine at what level of balance the center of gravity shifting is performed, for example, in such a manner as "left and right balance: 80 points", and "fore and aft balance: 72 points" for each of the left and right, and the fore and aft. These estimation results at the estimation unit 56 are stored in the storage unit 55. That is, the storage unit 55 is used as an estimation storage unit for storing the results of estimation at the estimation unit 56.

The comparison unit 591 is configured to compare the current result of estimation by the deviation estimation unit 56 with the previous result of estimation by the deviation estimation unit 56. For example, the comparison unit 591 reads out from the storage unit 55 the estimation results of the estimation unit 56 obtained in each setting mode before and after the training mode, and compares both the estimation results in the setting mode after the training mode. Here, the comparison unit 591 may quantitatively evaluate and numerically determine the relative comparison result of the estimation results after the training mode with respect to the estimation result before the training mode, or qualitatively evaluate it.

Moreover, the comparison unit 591 is configured to compare the results (current and previous results) of estimation by the center of gravity shifting estimation unit 58.

For example, the comparison unit 591 is configured to perform the comparison regarding the shifting distance per unit time (comparison of the current and previous estimation results by the center of gravity shifting estimation unit 58). The shifting distance per unit time is defined by a track length (distance between center of gravity positions).

Note that the comparison unit 591 may be configured to perform the above described comparison regarding the degree of spread. The degree of spread is defined by a sum of distances between the center of gravity position and the origin.

Moreover, the comparison unit 591 may be configured to perform the above described comparison regarding the areas of circumscribed rectangles surrounding regions through which a center of gravity passes.

Moreover, the comparison unit 591 may be configured to perform the above described comparison regarding a ratio of the areas of the above described circumscribed rectangles. The ratio of the areas of the above described circumscribed rectangles is, for example, a ratio of the areas of the above described circumscribed rectangles for the fore and aft, and the left and right.

Moreover, the comparison unit 591 may be configured to perform the comparison regarding an average velocity until when the operation icon 32 reaches the target icon 31. The average velocity is obtained by dividing the distance in which the center of gravity is shifted until when the operation icon 32 reaches the target icon 31 by the time elapsed from when the target icon 31 appears until when the operation icon 32 reaches the target icon 31.

The presentation unit 592 is configured to present the result of comparison (the result of comparison at the deviation estimation unit 56 or the result of estimation at the center of gravity shifting estimation unit 58) by the comparison unit 591. For example, the presentation unit 592 presents a comparison result at the comparison unit 591 to the user 2 in the setting mode after the training mode. To be specific, the presentation unit presents the comparison result to the user 2 by causing the display device 3 to display a comparison result from the display processing unit 53, or causing a printer (not shown) connected to the control device 5A to print out the comparison result. When the display device 3 is simultaneously used as the presentation unit 592, a conceivable configuration is to cause a comparison result to be automatically displayed on the display screen 30 after the end of measurement of center of gravity position by the measurement device 4 in the setting mode.

As so far described, in the center of gravity shifting training system 1A of the present embodiment, the control device 5A further includes the comparison unit 591 configured to compare the comparison results at the estimation unit 56 in the setting mode before and after the training mode, and the presentation unit 592 configured to present the comparison result at the comparison unit 591.

In other words, the control device 5A further includes the comparison unit 591 and the presentation unit 592. The comparison unit 591 is configured to compare the result of current estimation by the center of gravity shifting estimation unit 56 and the result of previous estimation by the center of gravity shifting estimation unit 56. The presentation unit 592 is configured to present the result of comparison by the comparison unit 591.

According to the center of gravity shifting training system 1A of the present embodiment described so far, it is possible to compare the estimations of center of gravity shifting of the user 2 before and after the training mode at the comparison unit 591, and present the comparison result to the user 2. Therefore, the user 2 can know how much effect has been achieved by the center of gravity shifting training performed in the training mode, and fully understand the need and effect of the center of gravity shifting training.

Moreover, in the center of gravity shifting training system 1A of the present embodiment, the comparison unit 591 numerically determines a comparison result, and the presentation unit 592 causes the display processing unit 53 to display the comparison result at the comparison unit 591 in the setting mode after the training mode. That is, the comparison unit 591 is configured to represent a result of comparison by a numerical value, and the presentation unit 592 is configured to cause the result of comparison to be displayed on the display screen 30.

In this way, the configuration in which the comparison unit 591 numerically determines a comparison result and the presentation unit 592 causes the display processing unit 53 to display the comparison result at the comparison unit 591 in the setting mode after the training mode allows the user 2 to quantitatively grasp the effect of the center of gravity shifting training. Moreover, since there is no need of using a separate display and printer etc. to present the comparison result to the user 2, it is possible to seek the simplification of system configuration.

Other configurations and functions of the center of gravity shifting training system 1A of the present embodiment are similar to those of the center of gravity shifting training system 1 of the first embodiment.

Third Embodiment

Figure 8:
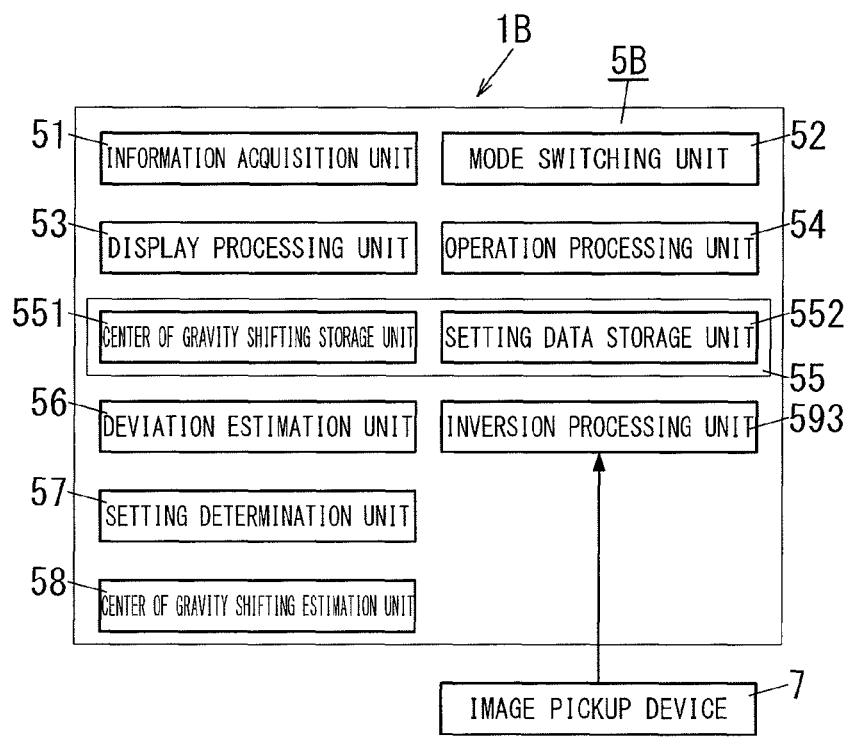
FIG. 8 is a schematic diagram illustrating a partially omitted system configuration of a center of gravity shifting training system of the third embodiment.

The center of gravity shifting training system 1B of the present embodiment differs from the center of gravity shifting training system 1 of the first embodiment in that there is no half mirror 6 provided as shown in FIG. 8. Moreover, in the center of gravity shifting training system 1B of the present embodiment, there is provided an image pickup device 7 which is disposed in front of the user 2 and whose lens is orientated so as to pick up an image of the user 2 from the front.

That is, the center of gravity shifting training system 1B of the present embodiment includes the display device 3, the measurement device 4, the control device 5B, and the image pickup device 7. Note that the display device 3 and the measurement device 4 are omitted in FIG. 8.

The image pickup device 7 is configured to shoot the user 2 and create an image of the user 2 in the training period.

The control device 5B includes an inversion processing unit 593 in addition to the mode switching unit 52, the information acquisition unit 51, the center of gravity position storage unit 551, the deviation estimation unit 56, the setting determination unit 57, the setting data storage unit 552, the operation processing unit 54, the display processing unit 53B, and the center of gravity shifting estimation unit 58.

The inversion processing unit 593 is configured to produce a mirror-reversed image by left-right inverting an image of the user 2 produced at the image pickup device 7.

The display processing unit 53B is configured to display a user image based on the image of the user 2 produced at the image pickup device 7 on the display screen 30. In the present embodiment, the display processing unit 53B is configured to display the mirror-reversed image produced at the inversion processing unit 593 on the display screen 30. That is, the user image is the mirror-reversed image produced at the inversion processing unit 593.

The image pickup device 7 is installed at a height position of the eyes of the user 2 on the front side (the user 2 side) of the display device 3 by utilizing, for example, a camera stand, etc. Further, the image pickup device 7 has its tilt angle and pan angle to be adjusted such that the whole body of the user 2 is included in the field of view, and the center line in the left and right direction of the body of the user 2 when the user 2 is in an upright position coincides with the center line of left and right direction of a picked up picture.

The above described adjustment of the position and orientation of the image pickup device 7 is performed as the initial setting after the standing position and the height of the eye line etc. of the user 2 are determined. As a result of this, the image pickup device 7 is allowed to pick up a dynamic image which reflects the whole body of the user 2 (hereafter, referred to as a "whole body picture").

The control device 5B is connected to both of the display device 3 and the image pickup device 7, and has a function of processing a picture picked up by the image pickup device 7 and causing the display device 3 to display the picture. To be specific, the control device 5B has the inverse processing unit 593 configured to acquire a whole body picture from the image pickup device 7 and reverse the acquired whole body picture from left to right to produce an inverted picture (mirror-reversed image). Further, the control device 5B causes the display device 3 to display the inverted picture along with the operation icon 32 and the target icon 31 at the display processing unit 53B such that the center line in the left and right direction of the inverted picture coincides with the center line in the left and right direction of the display screen 30.

As a result of this, a whole body picture of the user 2 is left-right inverted like a mirror image reflected on a mirror and is displayed along with the operation icon 32 and the target icon 31 on the display screen 30 of the display device 3. The inverted picture may be displayed so as to be overlapped with the operation icon 32 and the target icon 31. However in such a case, the inverted picture is desirably displayed as a semi-transparent picture (having, for example, a transmissivity of 50%).

Here, the control device 5B processes (inverts) a picture inputted from the image pickup device 7 in real time (about 15 to 30 frames per one second) and outputs a picture signal to the display device 3. The display device 3 receives the picture signal from the control device 5B, and displays an inverted picture in real time. For that reason, a dynamic image which moves in accordance with the actual movement of the user 2 is displayed as an inverted picture on the display screen 30 of the display device 3.

That is, the center of gravity shifting training system 1B of the present embodiment can make the user 2 visually recognize an inverted picture displayed on the display device 3 and cause the user 2 to falsely perceive the inverted picture as a mirror image of its own, without presenting a mirror image which is optically formed.

The center of gravity shifting training system 1B of the present embodiment described so far further includes the image pickup device 7 configured to pick up a picture of the user 2, and the display processing unit 53B is configured to cause the display device 3 to display the picture of the user picked up by the image pickup device 7 along with the operation icon 32 and the target icon 31.

In other words, the center of gravity shifting training system 1B of the present embodiment includes the image pickup device 7 configured to create an image of the user 2 by photographing the user 2 during the training period, and the display processing unit 53B is configured to display the user image based on the image of the user 2 created at the image pickup device 7 on the display screen 30.

According to the center of gravity shifting training system 1B of the present embodiment described above, there is an advantage in that the configuration can be simplified owing to the omission of the half mirror compared with the center of gravity shifting training system 1 of the first embodiment. Furthermore, in the configuration of the present embodiment, if a display having a relatively large screen is preinstalled, the existing display can be used as the display device 3 even without newly providing a dedicated display, and therefore it is possible to reduce the introduction cost of the system.

Moreover, as another example of the present embodiment, a picture of the user 2 which is picked up by an image pickup device installed at other than the front of the user 2, for example, the side, the rear, or the above of the user 2 may be displayed along with the operation icon 32 and the target icon 31 by the display device 3 at the display processing unit 53B. For example, when a picture of the user 2 picked up from the side of the user 2 is displayed on the display screen 30, the user 2 can perform center of gravity shifting training while confirming the inclination of its own body in the fore and aft direction as well.

Here, a picture of the user 2 picked up from other than the front may be displayed side by side with the above described inverted picture, or may be solely displayed. Further, even in the configuration including a half mirror 6 (see FIG. 1), the configuration may be such that a picture of the user 2 picked up by the image pickup device 7 from other than the front is displayed on the display device 3. In this instance, a whole body image of the user 2 seen from the front is represented by a mirror image reflected on the half mirror 6, and an image of the user 2 seen from other than the front is represented by a picture picked up by the image pickup device 7.

As a result of that a picture of the user 2 picked up from other than the front is displayed along with the above described inverted picture or a mirror image reflected on the half mirror 6, the user 2 can confirm the posture of its own from a plurality of directions and can perform center of gravity shifting training in a more proper posture.

Other configurations and functions of the center of gravity shifting training system 1B of the present embodiment are similar to those of the center of gravity shifting training system 1 of the first embodiment.

Fourth Embodiment

Figure 9:
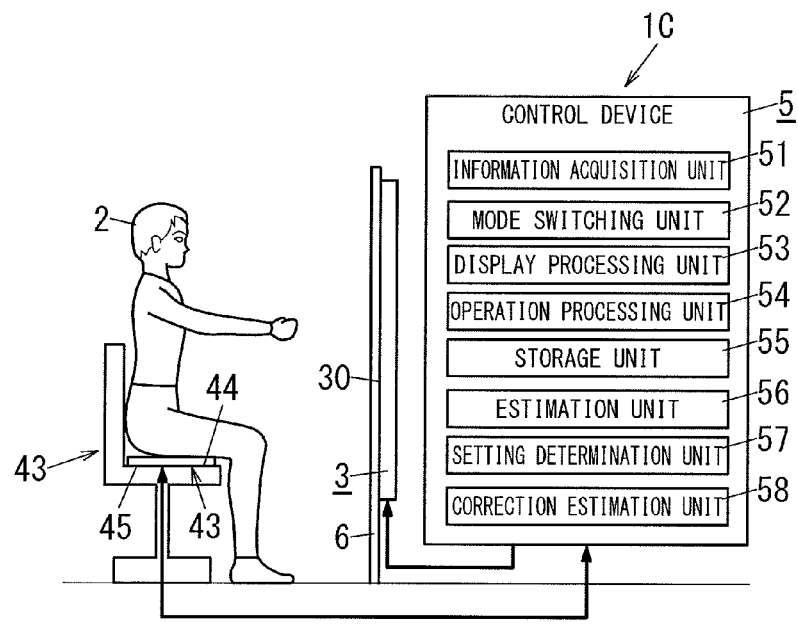
FIG. 9 is a schematic diagram illustrating the system configuration of a center of gravity shifting training system of the fourth embodiment.

The center of gravity shifting training system 1C of the present embodiment differs from the center of gravity shifting training system 1 of the first embodiment in that the measurement device 4C is provided in a chair 43 as shown in FIG. 9. That is, the center of gravity shifting training system 1C of the present embodiment includes the display device 3, the measurement device 4C, the control device 5, and the half mirror 6. In the present embodiment, the user 2 uses the center of gravity shifting training system 1C in a posture sitting in the chair 43 (sitting position).

The measurement device 4C is provided in the chair 43 which is installed in front of the half mirror 6. The measurement device 4C is placed on a seating face 44 of the chair 43, and is equipped with a sheet-shaped sensor sheet 45 for measuring the load applied to the seating face 44 from the buttocks of the user 2 sitting in the chair 43. That is, the measurement device 4C is configured to have the working face for receiving a load from the user 2 sitting in the chair 43, and measure the center of gravity position of the user 2 in the working face. In the present embodiment, the working face is the upper face of the sensor sheet 45. The sensor sheet 45 is configured such that a plurality of load sensors (not shown) for measuring the magnitude of load respectively applied from the user 2 are two-dimensionally arranged in a horizontal plane such that 3 or more load sensors are not aligned in one line and load sensors are separated from each other as far as possible in the horizontal plane.

In the present embodiment, the measurement device 4C measures the center of gravity position of the upper body of the user 2 on the seating face 44 by evaluating the load applying to each load sensor respectively, as the center of gravity position in the horizontal plane of the user 2 sitting in the chair 43. That is, if the upper body of the user 2 is not inclined in the fore and aft direction or the left and right direction, the proportion of load in each of the fore and aft direction and the left and right direction becomes equal, and the center of gravity position of the user 2 will be located at the center of the seating face 44.

The measurement device 4C measures the deviation of load in real time for each of the fore and aft direction and the left and right direction with reference to a state in which the center of gravity position is located at the center of the seating face 44, and evaluates the center of gravity position in the horizontal plane according to the deviation. In the present embodiment, the measurement device 4C evaluates, as the center of gravity position, the coordinate position of the center of gravity of the user 2 in two-dimensional orthogonal coordinate system in which it is supposed that the left and right direction of the user 2 in a state of facing the half mirror 6 is an X axis, the fore and aft direction is a Y axis, and the center position of the seating face 44 is (X, Y)=(0, 0).

In this way, the measurement device 4C measures the center of gravity position of the user 2 in the horizontal plane in real time and outputs the measurement result (center of gravity position) to the control device 5. For that reason, for example, if the user 2 leans its upper body to the right side while sitting in the chair 43, thereby shifting the center of gravity position to the right, the operation icon 32 on the display screen 30 (see FIGS. 3 and 4) is shifted to the right in accordance with the center of gravity shifting by the operation processing unit 54.

According to the center of gravity shifting training system 1C of the present embodiment described so far, the user 2 can perform the center of gravity shifting training even in a state of sitting in the chair 43, and there is an advantage that even a person whose walking is impaired due to disease or injury is allowed to perform the training of center of gravity shifting.

Other configurations and functions of the center of gravity shifting training system 1C of the present embodiment are similar to those of the center of gravity shifting training system 1 of the first embodiment.

Moreover, each of the configurations of the center of gravity shifting training systems 1A, 1B, and 1C of the second embodiment, the third embodiment, and the fourth embodiment may be appropriately combined.

Fifth Embodiment

Previously, there is proposed a system including a measurement device (balance detection device) disposed at the feet of a user (client) for measuring the proportion of load in the fore and the aft, and the left and the right of the user, in which a picture indicating the center of gravity position of the user which is evaluated from the output of the measurement device is displayed by a display device (for example, see document 2, "JP 2009-277195 A"). Using the system described in document 2 allows a user to learn a correct posture, in which the center of gravity is located at the center, by correcting the posture such that the center of gravity position coincides with the target position.

However, in the system described in document 2, although a training to reduce the fluctuation of the center of gravity position from a correct posture is made possible by a feedback of the center of gravity position to the user, a training of the user to learn a smooth center of gravity shifting needed for walking etc. is difficult. That is, although the system described in document 2 can display the shifting track of the center of gravity position, etc., it is difficult to estimate whether or not a smooth center of gravity shifting is performed from the shifting track of the center of gravity position, and the system is not adequate to be used for the training to learn a smooth center of gravity shifting.

Therefore, it is preferable that the center of gravity shifting training system enables the training to allow a user to learn a smooth center of gravity shifting.

Figure 10:
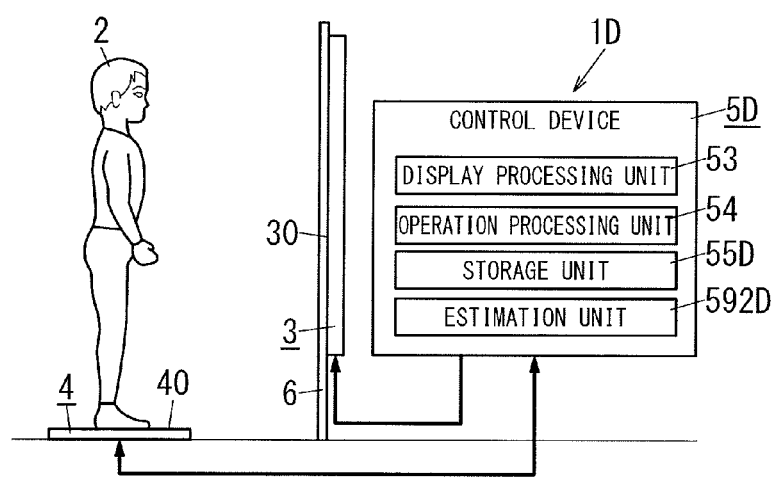
FIG. 10 is a schematic diagram illustrating the system configuration of a center of gravity shifting training system of the fifth embodiment.

The center of gravity shifting training system 1D of the present embodiment includes the display device 3, the measurement device 4, the control device 5D, and the half mirror 6 as shown in FIG. 10.

Figure 11:
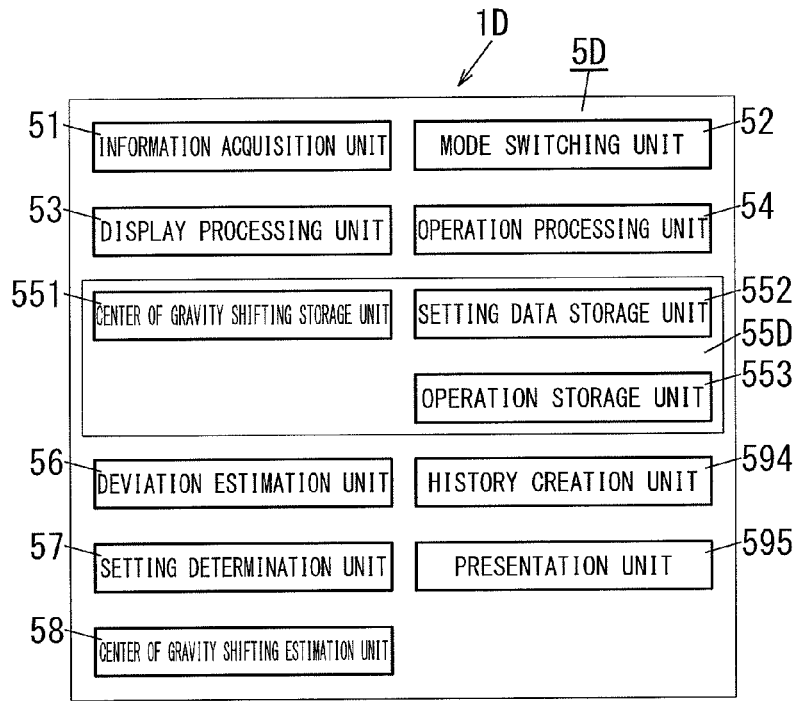
FIG. 11 is a schematic diagram illustrating a partially omitted system configuration of the center of gravity shifting training system of the fifth embodiment.

The control device 5D includes a history creation unit 594 and a presentation unit (history presentation unit) 595 in addition to the information acquisition unit 51, the mode switching unit 52, the display processing unit 53, the operation processing unit 54, the storage unit 55D, the estimation unit (deviation estimation unit) 56, the setting determination unit 57, and the center of gravity shifting estimation unit 58 as shown in FIG. 11. Moreover, the storage unit 55D includes an operation storage unit 553 in addition to the center of gravity position storage unit 551 and the setting data storage unit 552.

The history creation unit 594 is configured to create an operation history indicating the history of the position and movement of the operation image 32 based on the position of the operation image 32 determined at the operation processing unit 54 in the training period.

The operation storage unit 553 is configured to store the operation history created at the history creation unit 594.

The history presentation unit 595 is configured to present the operation history stored in the operation storage unit 553.

Note that the information acquisition unit 51, the mode switching unit 52, the deviation estimation unit 56, the setting determination unit 57, the center of gravity shifting estimation unit 58, and the history creation unit 594 are omitted in FIG. 10.

By the way, in the configuration described above, there may be no significant difference in the score between a case where the user 2 has scooped a goldfish of the target icon 31 without significantly performing center of gravity shifting, and a case where the user 2 has scooped a goldfish of the target icon 31 by actively performing center of gravity shifting. That is, since the user 2 may be able to wait the target icon 31 passing nearby the operation icon 32 and scoop a goldfish without significantly moving the operation icon 32, there may a case where such user 2 cannot be distinguished from the user 2 who has actively moved the operation icon 32 based on only the score.

Accordingly, in the center of gravity shifting training system 1D of the present embodiment, the storage unit 55D functions as the operation storage unit 553 for storing the history of the movement of the operation icon 32 in the display screen 30 as an operation history, and the control device 5D further includes the presentation unit (history presentation unit) 595 for presenting the operation history in the storage unit 55D to the user 2.

That is, the history in which the user 2 has moved the operation icon 32 on the display screen 30 by performing center of gravity shifting during the training period is stored in the storage unit 55D (operation storage unit 553) as the operation history. In the present embodiment, a shifting track, a track length (shifting amount), a shifting direction, a shifting velocity, an acceleration, etc. of the operation icon 32 in the display screen 30 are stored in the storage unit 55D (operation storage unit 553) as the operation history. The shifting track of the operation icon 32 is specified by representing the coordinate position of the operation icon 32 in time series, and the shifting velocity and the acceleration are periodically calculated from the relationship between the track length and time.

The presentation unit 595 presents the operation history stored in the storage unit 55D (operation storage unit 553) during the training period to the user 2 after the end of the training period. To be specific, the presentation unit 595 presents the operation history to the user 2 by causing a printer (not shown) connected to the control device 5D to print out the operation history, or controlling the display device 3 in such a manner to display the operation history. When the display device 3 is simultaneously used as the presentation unit 595, a conceivable configuration is to cause the operation history to be displayed on the display screen 30 after the end of the training period.

The information presented by the presentation unit 595 includes images respectively representing a shifting track and a shifting direction, and numerical values respectively representing a track length, a shifting velocity, an acceleration, for example. Regarding the shifting velocity, acceleration etc., numerical values representing an average value, a maximum value, and a minimum value during the training period may be presented. When such operation history is presented by the presentation unit 595, a person who is given the presentation, such as a user 2 or a therapist etc., can estimate the movement of the operation icon 32 in the display screen 30 based on the presented operation history. The movement of the operation icon 32 represents a center of gravity shifting performed by the user 2 during a training period, and therefore estimating the movement of the operation icon 32 will mean estimating the center of gravity shifting performed by the user 2.

In short, for example, when the shifting track in the operation history is deviated to the right side of the display screen 30, the person who is given the presentation of the operation history can make estimation such as that the user 2 is being able to cope with the center of gravity shifting to rightward, but is not being able to cope with the center of gravity shifting to leftward. Moreover, for example, when the shifting velocity in the operation history is extremely low, the person who is given the presentation can make estimation such as that the user 2 is not being able to cope with a rapid center of gravity shifting.

Here, using a standard operation history by an able-bodied person as the estimation criterion for the estimation of operation history will enable the person who is presented with the operation history to relatively estimate the center of gravity shifting of the user 2 with respect to the center of gravity shifting of a standard person. That is, the person who is given the presentation can evaluate the difference of numerical values representing a variation of shifting track, a track length, a shifting velocity, an acceleration, etc. by comparing the operation history presented at the presentation unit 595 with an estimation criterion, and quantitatively estimate the center of gravity shifting of the user 2. As the estimation criterion, an operation history in the past of the user 2 may be used and in this instance, it is possible to estimate how the center of gravity shifting has changed compared with that in the past on the same user 2, thereby enabling the estimation of the degree of progress in the center of gravity shifting training.

As so far described, the center of gravity shifting training system 1D of the present embodiment includes the display device 3 for displaying a picture on the display screen 30, the control device 5D configured to control the display device 3 to display a picture, and the measurement device 4 disposed at the feet of the user 2 facing the display screen 30 and configured to measure the center of gravity position of the user 2 in the horizontal plane. The control device 5D includes the display processing unit 53, the operation processing unit 54, the operation storage unit 553, and the presentation unit 595. The display processing unit 53 is configured to control the display device 3 to display the operation icon 32 and the target icon 31 which provides an object of tracing by the concerned operation icon 32. The operation processing unit 54 is configured to vary the position of the operation icon 32 in the display screen 30 based on the center of gravity position measured at the measurement device 4. The operation storage unit 553 is configured to store the history of the movement of the operation icon 32 in the display screen 30 as the operation history. The presentation unit 595 is configured to present the operation history.

In other words, the control device 5D further includes the history creation unit 594, the operation storage unit 553, and the presentation unit 595. The history creation unit 594 is configured to create an operation history indicating the history of the position and movement of the operation image 32 based on the position of the operation image 32 which is determined at the operation processing unit 54 in the training period. The operation storage unit 553 is configured to store the operation history created at the history creation unit 594. The presentation unit 595 is configured to present the operation history stored in the operation storage unit 553.

According to the center of gravity shifting training system 1D of the present embodiment described so far, there is an advantage that it is possible to make the user 2 perform the training to learn a smooth center of gravity shifting. To be more specific, it is possible to make the user 2 perform a center of gravity shifting in accordance with the movement of the target icon 31 so as to follow the target icon 31 on the display screen 30 by means of the operation icon 32. The history of the movement of the operation icon 32 at this moment is stored in the storage unit 55D (operation storage unit 553) as the operation history, and the operation history is fed back to the user 2 or a therapist etc. from the presentation unit 595. Therefore, the person who is presented with the operation history becomes able to estimate the center of gravity shifting performed by the user 2 during the training period based on the operation history. From this estimation result, the user 2 can fully understand the need and effect of the center of gravity shifting training.

Sixth Embodiment

Figure 12:
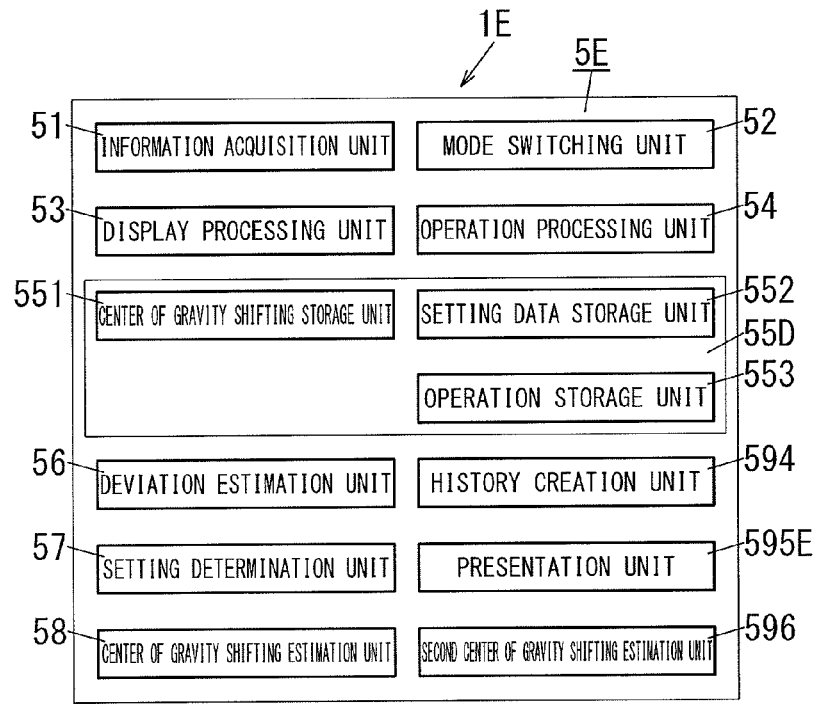
FIG. 12 is a schematic diagram illustrating a partially omitted system configuration of a center of gravity shifting training system of the sixth embodiment.

The center of gravity shifting training system 1E of the present embodiment differs from the center of gravity shifting training system 1D of the fifth embodiment in that the control device 5E has an estimation unit (second center of gravity shifting estimation unit) 596 configured to estimate the movement of the operation icon 32 in the display screen 30 based on the operation history, as shown in FIG. 12. The center of gravity shifting training system 1E of the present embodiment includes the display device 3, the measurement device 4, the control device 5E, and the half mirror 6. Note that the display device 3, the measurement device 4, and the half mirror 6 are omitted in FIG. 12.

The control device 5E includes the center of gravity shifting estimation unit (second center of gravity shifting estimation unit) 596 in addition to the information acquisition unit 51, the mode switching unit 52, the display processing unit 53, the operation processing unit 54, the storage unit 55D, the estimation unit (deviation estimation unit) 56, the setting determination unit 57, the center of gravity shifting estimation unit 58, the history creation unit 594, and the presentation unit 595E.

The center of gravity shifting estimation unit (second center of gravity shifting estimation unit) 596 is configured to perform the estimation of the center of gravity shifting of the user 2 based on the operation history stored in the operation storage unit 553. In the present embodiment, the estimation unit 596 estimates the movement of the operation icon 32 by comparing the operation history (images representing a shifting track and a shifting direction, and numerical values representing a track length, a shifting velocity, and an acceleration etc.) presented by the presentation unit 595E with an estimation criterion made up of a standard operation history by an able-bodied person prestored in the storage unit 55D. The movement of the operation icon 32 represents the center of gravity shifting performed by the user 2 during the training period. Therefore, the estimation unit 596 can estimate the center of gravity shifting performed by the user 2 by estimating the movement of the operation icon 32.

That is, for example, when the shifting track in the operation history is deviated to the right side of the display screen 30, the estimation unit 596 estimates that the user 2 is able to cope with the center of gravity shifting to rightward, but is not able to cope with the center of gravity shirting to leftward. Moreover, for example, when the shifting velocity in the operation history is extremely low, the estimation unit 596 estimates that the user 2 is not able to cope with a rapid center of gravity shifting.

Here, the estimation unit 596 numerically determines the differences of numerical values representing a variation of sifting track, a track length, a shifting velocity, an acceleration, etc. as an estimation point by comparing the operation history presented by the presentation unit 595E with an estimation criterion, and quantitatively estimate the center of gravity shifting of the user 2. Further, the estimation unit 596 may convert the estimation point into points on a 100-point scale as the estimation result. For example, as for the track length, the estimation point is increased with a decrease in the track length.

The storage unit 55D may store, for example, a standard operation history for each age, sex, height as the estimation criterion and, in this instance, the estimation unit 596 selects the estimation criterion to be used for estimation depending on the age, sex, and height of the user 2. Moreover, as the estimation criterion to be used for estimation by the estimation unit 596, an operation history of the user 2 in the past may be used and, in this instance, it is possible to estimate how the center of gravity shifting has changed compared with that in the past on the same user 2, thus allowing the estimation of the degree of progress in the center of gravity shifting training.

Moreover, in the present embodiment, since the target icon 31 is displayed so as to be shifted in the display screen 30, the operation icon 32 is operated so as to chase the target icon 31 moving around in the display screen 30. Accordingly, the estimation unit 596 is configured not only to estimate the movement of the operation icon 32 alone, but also to estimate the following performance of the operation icon 32 with respect to the target icon 31.

That is, the storage unit 55D functions as a target storage unit configured to store the history of movement of the target icon 31 in the display screen 30 as the target history, and the estimation unit 596 estimates the following performance of the operation icon with respect to the target icon, in which the following performance is evaluated by comparing the operation history in the storage unit 55D with the target history. In short, the history of the target icon 31 which has moved on the display screen 30 during the training period is stored in the storage unit 55D as the target history. In the present embodiment, the shifting track, track length (shifting amount), shifting direction, shifting velocity, acceleration, etc. of the target icon 31 in the display screen 30 are stored in the storage unit 55D as the target history. The shifting track of the target icon 31 is identified by representing the coordinate position (display position in the display screen 30) of the target icon 31 in time series, and the shifting velocity and acceleration are calculated periodically from the relation between the track length and time.

Here, the estimation unit 596 numerically determines the differences of the numerical values representing a variation of shifting track, a track length, a shifting velocity, an acceleration, etc. as the estimation point by comparing the operation history with the target history, and quantitatively estimate the following performance of the operation icon 32 with respect to the target icon 31. That is, the estimation unit (second center of gravity shifting estimation unit) 596 is configured to estimate the following performance of the operation image 32 with respect to the target image 31 based on the target history representing the history of the position of the target image 31, and the operation history. In the present embodiment, since the target image 31 is displayed to be shifted on the display screen 30, the target history indicates the history of the position and movement of the target image 31. When the target image 31 is displayed in order at a predetermined position of the display screen 30, the target history indicates the position of the target image 31.

The position and movement (shifting pattern) of the target icon 31 depend on the setting data. When the setting data uniquely determines the shifting pattern of the target icon 31 (when the target icon 31 is not shifted randomly), the estimation unit 596 estimates the following performance of the operation image 32 with respect to the target image 31 based on the operation history and the setting data. On the other hand, when the setting data does not uniquely determine the shifting pattern of the target icon 31 (when the target icon 31 is randomly shifted), the estimation unit 596 creates a target history indicating the history of the position and movement of the target image 31, and estimates the following performance of the operation image 32 with respect to the target image 31 based on the created target history and the operation history. Note that regardless of the content of the setting data, the estimation unit 596 may create a target history and estimate the following performance of the operation image 32 with respect to the target image 31 based on the created target history and the operation history.

The estimation result of the estimation unit 596 is presented along with the operation history by the presentation unit 595E after the end of the training period. That is, the presentation unit 595E is configured to present the result of the estimation by the second center of gravity shifting estimation unit 596 along with the operation history.

As so far described, in the center of gravity shifting training system 1E of the present embodiment, the control device 5E further includes an estimation unit (second center of gravity shifting estimation unit) 596 for estimating the movement of the operation icon 32 in the display screen 30 based on the operation history. The presentation unit 595E is configured to present the estimation result of the estimation unit 596 along with the operation history.

In other words, the control device 5E includes the (second) center of gravity shifting estimation unit 596, and the center of gravity shifting estimation unit 596 is configured to estimate the center of gravity shifting of the user 2 based on the operation history stored in the operation storage unit 553. The presentation unit 595E is configured to present the result of the estimation by the center of gravity shifting estimation unit 596 along with the operation history.

According to the center of gravity shifting training system 1E of the present embodiment described so far, the movement of the operation icon 32 representing the center of gravity shifting performed by the user 2 is automatically estimated by the estimation unit 596, and the estimation result is fed back to the user 2 from the presentation unit 595E. Therefore, the user 2 will become able not only to know the operation history representing the center of gravity shifting of its own, but also to understand how the operation history is estimated in the light of the estimation criterion. That is, the user 2 can know that, for example, the shifting of the center of gravity position to forward (forward inclination) has reached a standard value, but the shifting of the center of gravity position to rearward (rearward inclination) is lower than the standard value, and fully understand the need and effect of the center of gravity shifting training.

Moreover, in the center of gravity shifting training system 1E of the present embodiment, the display processing unit 53 controls the display device 3 in such a manner to display the target icon 31 such that the target icon 31 is shifted in the display screen 30. The control device 5E further includes the target storage unit (storage unit) 55D configured to store the history of the movement of the target icon 31 in the display screen 30 as the target history. The estimation unit 596 is configured to estimate the following performance of the operation icon 32 with respect to the target icon 31, in which the following performance is evaluated by comparing the operation history with the target history.

In other words, the center of gravity shifting estimation unit (second center of gravity shifting estimation unit) 596 is configured to estimate the following performance of the operation image 32 with respect to the target image 31 based on the target history indicating the history of the position of the target image 31 and the operation history.

According to the center of gravity shifting training system 1E of the present embodiment, since the estimation unit 596 estimates the following performance of the operation icon 32 with respect to the target icon 31 as well, it can estimate to what extent the user 2 is being able to chase the target icon 31 which is shifted in the display screen 30. As a result of the estimation result being fed back to the user 2 from the presentation unit 595E, the user 2 can recognize the explosive force of its own, and the like.

As an application example of the present embodiment, the setting determination unit 57 may be configured to correct the setting data stored in the setting data storage unit 552 according to the result of the estimation by the (second) center of gravity shifting estimation unit 596. That is, the control device 5E may have the setting updating unit (setting determination unit) 57 for (automatically) changing the setting data (setting value) for determining the position (including movement) of the target icon 31 in the display screen 30 according to the estimation result of the estimation unit 596. In this configuration, the position (including the movement) of the target icon 31 in the display screen 30 will be automatically changed according to the estimation result at the estimation unit.

That is, when it is estimated at the estimation unit 596 that, for example, the user 2 is not being able to cope with the center of gravity shifting to leftward, the setting updating unit 57 changes the shifting pattern of the target icon 31 such that the target icon 31 is displayed predominantly on the right side of the display screen 30. To be specific, the setting updating unit 57 limits the range in which the target icon 31 is displayed in the display screen 30 into the right half of the display screen 30, or changes the shifting track of the target icon 31 such that the target icon 31 predominantly passes through the right half of the display screen 30.

Moreover, when a high estimation is obtained at the estimation unit 596, the setting updating unit 57 raises the shifting velocity of the target icon 31 or increase the number of target icons 31 in an effort to increase the level of difficulty of the center of gravity shifting. On the other hand, when a low estimate is obtained by the estimation unit 596, the setting updating unit 57 lowers the shifting velocity of the target icon 31, or changes the shifting pattern of the target icon 31 to a monotonous shifting pattern.

As a result of this, the center of gravity sifting training system 1E has an advantage that it can make the user 2 to perform an appropriate exercise in accordance with the learning level of the center of gravity shifting of the user 2.

Other configurations and functions of the center of gravity shifting training system 1E of the present embodiment are similar to those the center of gravity shifting training system 1D of the fifth embodiment.

The invention claimed is:

1. A center of gravity shifting training system comprising:
 a display device having a display screen for displaying an image;
 a measurement device, having a working face for receiving a load from a user, that measures a center of gravity position of the user in said working face; and
 a control device having two operation modes including a training mode, in which an operation image which is shifted according to the center of gravity position measured at said measurement device and a target image which indicates a destination of the operation image are displayed on said display screen, and a setting mode in which setting data which indicates the position of the target image in said display screen is prepared,
 wherein
 said control device comprises:
 a mode switch that switches the operation modes of said control device between the training mode and the setting mode;
 an information acquirer that acquires the center of gravity position from said measurement device;
 a center of gravity position storage that stores the center of gravity position acquired by said information acquirer during a setting period in which said control device is in the setting mode;
 a deviation estimator that estimates, during the setting period, a deviation of the center of gravity position based on the center of gravity position stored in said center of gravity position storage;
 a setting determiner that determines, during the setting period, the setting data, indicating a position of the target image, according to the estimation of the deviation of the center of gravity position by said deviation estimator;
 a setting data storage that stores the setting data prepared at said setting determiner;
 an operation processor that determines a display position of the operation image in the display screen according to the center of gravity position acquired by the information acquirer; and
 a display processor that displays the operation image at the display position determined at said operation processor, and displays the target image in the display screen based on the setting data stored in said setting data storage, in a training period in which said control device is in the training mode.

2. A center of gravity shifting training system as set forth in claim 1, wherein
 said control device further comprises a center of gravity shifting estimator,
 said center of gravity shifting estimator performs estimation of center of gravity shifting of the user based on a position of the operation image in the training period, and
 said setting determiner corrects the setting data stored in said setting data storage according to a result of the estimation by said center of gravity shifting estimator.

3. A center of gravity shifting training system as set forth in claim 1, wherein
 said display processor displays the center of gravity position stored in said center of gravity position storage on the display screen in the setting period.

4. A center of gravity shifting training system as set forth in claim 2, wherein
 said control device comprises a comparator and a presenter,
 said comparator performs a comparison between a result of a current estimation by said center of gravity shifting estimator and a result of a previous estimation by said center of gravity shifting estimator, and
 said presenter presents a result of the comparison by said comparator.

5. A center of gravity shifting training system as set forth in claim 4, wherein
 said comparator represents the result of the comparison by a numerical value, and
 said presenter displays the result of the comparison on said display screen.

6. A center of gravity shifting training system as set forth in claim 1, wherein
 said control device comprises a history creator, an operation storage, and a presenter, wherein
 said history creator creates an operation history indicating a history of position and movement of the operation image based on a position of the operation image determined at said operation processor in the training period, said operation storage stores the operation history created by said history creator, and said presenter presents the operation history stored in said operation storage.

7. A center of gravity shifting training system as set forth in claim 6, wherein said control device further comprises a center of gravity shifting estimator, said center of gravity shifting estimator performs estimation of center of gravity shifting of the user based on the operation history stored in said operation storage, and said presenter presents a result of the estimation by said center of gravity shifting estimator along with the operation history.

8. A center of gravity shifting training system as set forth in claim 7, wherein said center of gravity shifting estimator estimates a following performance of the operation image with respect to the target image, based on a target history, indicating a history of the position of the target image, and the operation history.

9. A center of gravity shifting training system as set forth in claim 7, wherein said setting determiner corrects the setting data stored in said setting data storage unit according to a result of the estimation by said center of gravity shifting estimator.

10. A center of gravity shifting training system as set forth in claim 1, wherein a half mirror is positioned in front of said display screen, and a thickness direction of the half mirror coincides with a normal direction of the display screen.

11. A center of gravity shifting training system as set forth in claim 1, further comprising an image pickup device that images the user during the training period to create an image of the user, wherein said display processor displays a user image based on the image of the user created at said image pickup device on said display screen.

* * * * *